(12) United States Patent
Zhang et al.

(10) Patent No.: US 11,198,712 B2
(45) Date of Patent: *Dec. 14, 2021

(54) SECRETORY PROTEIN

(71) Applicant: Shanghai Clear Fluid Biomedical Science Co., Ltd., Shanghai (CN)

(72) Inventors: Yinghao Zhang, Shanghai (CN); Jingpeng Fu, Shanghai (CN); Jia Wan, Shanghai (CN)

(73) Assignee: Shanghai Clear Fluid Biomedical Science Co., Ltd., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/028,769

(22) Filed: Sep. 22, 2020

(65) Prior Publication Data

US 2021/0009644 A1 Jan. 14, 2021

Related U.S. Application Data

(60) Division of application No. 16/145,251, filed on Sep. 28, 2018, now Pat. No. 10,815,282, which is a continuation-in-part of application No. PCT/CN2017/090785, filed on Jun. 29, 2017.

(30) Foreign Application Priority Data

Jul. 4, 2016 (CN) .......................... 201610519038.9

(51) Int. Cl.
| | |
|---|---|
| *C07K 14/47* | (2006.01) |
| *A61P 25/28* | (2006.01) |
| *C07K 19/00* | (2006.01) |
| *C12N 15/861* | (2006.01) |
| *A61K 38/17* | (2006.01) |
| *C12N 15/85* | (2006.01) |
| *C12N 5/10* | (2006.01) |
| *A61K 45/00* | (2006.01) |
| *A61K 48/00* | (2006.01) |
| *C12N 15/867* | (2006.01) |

(52) U.S. Cl.
CPC .............. *C07K 14/47* (2013.01); *A61K 38/17* (2013.01); *A61K 45/00* (2013.01); *A61K 48/00* (2013.01); *A61P 25/28* (2018.01); *C07K 19/00* (2013.01); *C12N 5/10* (2013.01); *C12N 15/85* (2013.01); *C12N 15/861* (2013.01); *C12N 15/867* (2013.01)

(58) Field of Classification Search
None
See application file for complete search history.

(56) References Cited

U.S. PATENT DOCUMENTS 10,815,282 B2 * 10/2020 Zhang ..................... A61P 25/28

FOREIGN PATENT DOCUMENTS

WO WO-2018006750 A1 1/2018

OTHER PUBLICATIONS

Database Geneseq [Online] Sep. 30, 2015 (Sep. 30, 2015), "pan paniscus split hand/foot malformation (ectrodactyly) type 1 (SHFM1), transcript, transcript variant XI, mRNA",retrieved from EBI, HINXTON UK Database accession no.*
Database UniProt [Online] May 31, 2011 (May 31, 2011), "SubName: Full=26S proteasome complex subunit SEM1 [ECO:0000313| Ensembl:ENSP00000409481};", retrieved from EBI accession No. UNIPROT:F2Z309 Database accession No. F2Z309.*
Zhang et al. "DSSylation, a novel protein modification targets proteins induced by oxidative stress, and facilitates their degradation in cells", Protein & Cell, Springer Asia, Beijing, CN, vol. 5, No. 2, Feb. 11, 2014 (Feb. 11, 2014), pp. 124-140, XP035734439JSSN: 1674-800X, DOI: 10.1007/SI3238-013-0018-8.*
Gong "DSSylation, a Novel Guide for Protein Degradation",Protein Cell, vol. 5, No. 2, Jan. 29, 2014 (Jan. 29, 2014), XP035734440.*
Cao, W. et al. AOPPs and the progression of kidney disease. Kidney Int Suppl (2011). Nov. 2014;4(1):102-106.
Chang, L. et al. Protection against β-amyloid-induced synaptic and memory impairments via altering β-amyloid assembly by bis(heptyl)-cognitin. Sci Rep. Jul. 21, 2015;5:10256. doi: 10.1038/srep10256.
Choe, Y.J. et al. Failure of RQC machinery causes protein aggregation and protectoxic stress. Nature. Mar. 10, 2016; 531(7593):191-5. doi: 10.1038/nature16973. Epub Feb. 29, 2016.
Dobson, CM. Protein misfolding, evolution and disease. Trends Biochem Sci. Sep. 1999;24(9):329-32.
Dunlop, et al. Proteins containing oxidized amino acids induce apoptosis in human monocytes. Biochem J. Apr. 1, 2011;435(1):207-216. doi: 10.1042/BJ20100682.
Extended European Search Report for EP17823562.8 dated Jun. 27, 2019.

(Continued)

*Primary Examiner* — Maury A Audet
(74) *Attorney, Agent, or Firm* — Wilson Sonsini Goodrich & Rosati

(57) ABSTRACT

The disclosure of the present application relates to a secretory deleted split hand/split foot 1 (sDSS1) protein, the amino acid sequence thereof, the nucleic acid sequence thereof, and the applications of the same. The sDSS1 protein is a secretory protein from higher primate, and can be detected in human serum and cerebral spinal fluid (CSF). The sDSS1 protein can form conjugate with oxidized protein under nonenzymatic condition or with amyloid-beta (Aβ) polypeptide to reduce formation of Aβ oligomer. The addition of sDSS1 protein to culture medium can shield the cytotoxicity induced by oxidized protein, Aβ oligomer, amylin oligomer and glycosylated protein, so as to protect the cells against these toxoproteins. The sDSS1 protein can prolong survival time of senescence-accelerated mice significantly. The protein can be used to prevent and treat the diseases induced by oxidized protein, glycated protein, Aβ protein accumulation, amylin protein accumulation or excessive formation or accumulation of other pathogenic proteins with similar features, and has important potential in biological medicine.

15 Claims, 20 Drawing Sheets

Specification includes a Sequence Listing.

(56) References Cited

OTHER PUBLICATIONS

Fernandez, MS. Human IAPP amyloidogenic properties and pancreatic β-cell death. Cell Calcium. Nov. 2014;56(5):416-27. doi: 10.1016/j.ceca.2014.08.011. Epub Aug. 27, 2014.

Fonteneau, et al. Serum-Mediated Oxidative Stress From Systemic Sclerosis Patients Affects Mesenchymal Stem Cell Function. Front Immunol. Sep. 1, 2017;8:988. doi: 10.3389/fimmu.2017.00988. eCollection 2017.

GenBank accession No. XM_008961980.1, retrieved from https://www.ncbi.nlm.nih.gov/nuccore/XM_008961980.1, retrieved on Jul. 27, 2017, Sep. 30, 2015.

GenBank accession No. XP_008960228.1, retrieved from https://www.ncbi.nlm.nih.gov/protein/XM_008960228.1, retrieved on Jul. 27, 2017, Sep. 30, 2015.

Gong, C.X. DSSylation, a novel guide for protein degradation? Protein Cell. Feb. 2014;5(2):91-93. doi: 10.1007/s13238-014-0020-9.

International search report dated Oct. 9, 2017 for PCT/CN2017/090785.

Kim, H.Y. et al. EPPS rescues hippocampus-dependent cognitive deficits in APP/PS1 mice by disaggregation of amyloid-β oligomers and plaques. Nat Commun 6, 8997 (2015) doi:10.1038/ncomms9997.

Liang, M. et al. Advanced oxidation protein products promote NADPH oxidase-dependent β-cell destruction and dysfunction through the Bcl-2/Bax apoptotic pathway. Lab Invest. Jul. 2017;97(7):792-805. doi: 10.1038/labinvest.2017.24. Epub Mar. 6, 2017.

Liang, M. et al. Increased plasma advanced oxidation protein products is an early marker of endothelial dysfunction in type 2 diabetes patients without albuminuria. J Diabetes. Sep. 2014;6(5):417-26. doi: 10.1111/1753-0407.12134. Epub Mar. 27, 2014.

Lim, Y.A. et al. Aβ and human amylin share a common toxicity pathway via mitochondrial dysfunction. Proteomics. Apr. 2010;10(8):1621-33. doi: 10.1002/pmic.200900651.

Ma, et al. Identification of the deleted in split hand/split foot 1 protein as a novel biomarker for human cervical cancer. Carcinogenesis. Jan. 2013;34(1):68-78. doi: 10.1093/carcin/bgs279. Epub Sep. 28, 2012.

Notice of Allowance dated Jul. 28, 2020 for U.S. Appl. No. 16/145,251.

Office action dated Apr. 3, 2020 for U.S. Appl. No. 16/145,251.

Office action dated Dec. 13, 2019 for U.S. Appl. No. 16/145,251.

Ott, C. et al. Protein oxidation and proteolytic signalling in aging. Curr Pharm Des. 2014;20(18):3040-51.

Rezano, A. et al. Breast cancers with high DSS1 expression that potentially maintains BRCA2 stability have poor prognosis in the relapse-free survival. BMC Cancer. Dec. 1, 2013;13:562. doi: 10.1186/1471-2407-13-562.

Sadigh-Eteghad, S et al. Amyloid-beta: a crucial factor in Alzheimer's disease. Med Princ Pract. 2015;24(1):1-10. doi: 10.1159/000369101. Epub Nov. 27, 2014.

Simm, A. et al. Protein glycation—Between tissue aging and protection. Exp Gerontol. Aug. 2015;68:71-5. doi: 10.1016/j.exger.2014.12.013. Epub Dec. 20, 2014.

Turell, et al. Mechanisms and consequences of protein cysteine oxidation: the role of the initial short-lived intermediates. Essays Biochem. Feb. 17, 2020;64(1):55-66. doi: 10.1042/EBC20190053.

UniProtKB—F2Z309 (F2Z309_HUMAN). 26S proteasome complex subunit SEM1. Retrieved from https://www.uniprot.org/uniprot/F2Z309. Last modified: May 31, 2011—v1.

Winblad, B. et al. Safety, tolerability, and antibody response of active Aβ immunotherapy with CAD106 in patients with Alzheimer's disease: randomised, double-blind, placebo-controlled, first-in-human study. Lancet Neurol. Jul. 2012;11(7):597-604. doi: 10.1016/S1474-4422(12)70140-0. Epub Jun. 6, 2012.

Zhang, Y. et al. DSSylation, a novel protein modification targets proteins induced by oxidative stress, and facilitates their degradation in cells. Protein Cell. Feb. 2014;5(2):124-40. doi: 10.1007/s13238-013-0018-8. Epub Feb. 11, 2014.

Zhao, LN. et al. The toxicity of amyloid β oligomers. Int J Mol Sci. 2012;13(6):7303-27. doi: 10.3390/ijms13067303. Epub Jun. 13, 2012.

\* cited by examiner

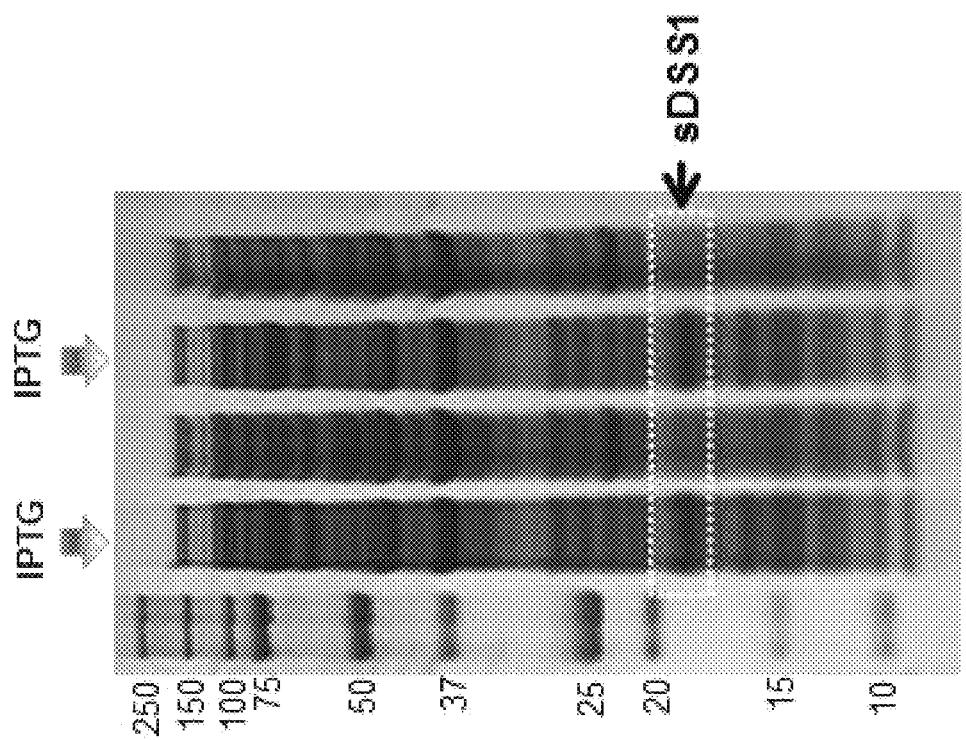

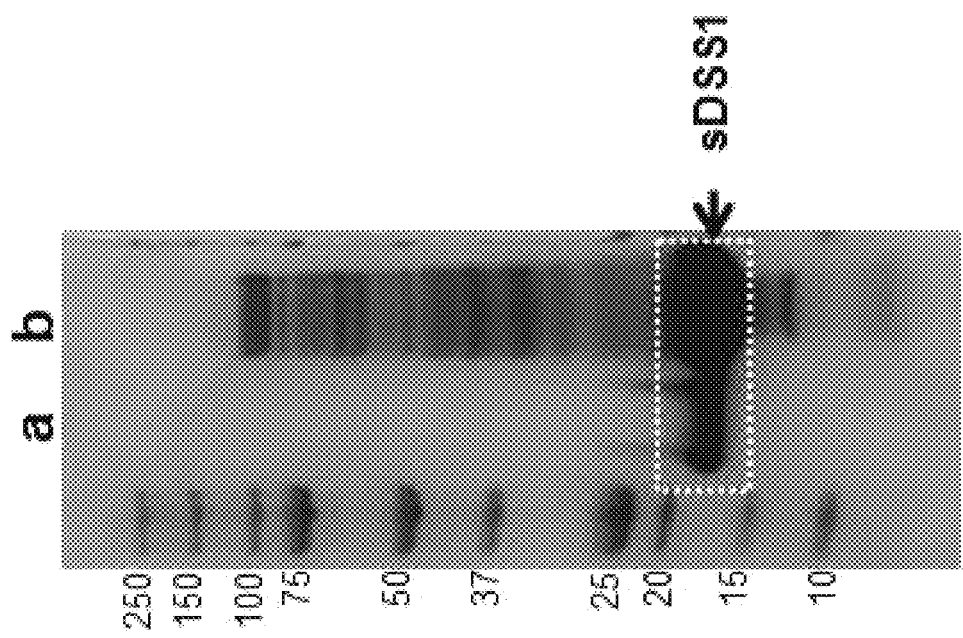

SECRETORY PROTEIN

CROSS-REFERENCE TO RELATED APPLICATION

The present application is a division of U.S. Non-Provisional patent application Ser. No. 16/145,251, filed Sep. 28, 2018, which is continuation-in-part application of PCT Application No. PCT/CN2017/090785 filed on Jun. 29, 2017, which claims the benefit of Chinese Patent Application No. 201610519038.9 filed on Jul. 4, 2016, the disclosure of which is hereby incorporated by reference in their entirety.

REFERENCE TO SEQUENCE LISTING

The instant application contains a Sequence Listing which has been submitted electronically in ASCII format and is hereby incorporated by reference in its entirety. Said ASCII copy created on Sep. 21, 2020, is named 57275701401_SL.txt and is 14,572 bytes in size.

BACKGROUND

The present application relates generally to a secretory protein, the secretory protein can be used to prepare the drugs for preventing and treating the diseases induced by excessive formation or excessive accumulation of junk proteins.

DESCRIPTION OF RELATED ART

In normal physiological activities, the organism generates lots of junk proteins, including oxidized protein, glycosylated protein and some abnormal spliced proteins (polypeptide). The organism retains multiple mechanisms for removing junk proteins to maintain normal physiological function. However, the aging or diseases will induce excessive formation of junk proteins or degrade the organism's ability to remove junk proteins, so that lots of junk proteins accumulate. The abnormal accumulation of junk proteins inside or outside the cells is the key mechanism inducing a series of diseases. The typical diseases include chronic kidney disease, Alzheimer's disease (AD), Huntington's disease, diabetes complications and so on[1-5]. The accumulation of oxidized protein, glycated protein or other junk proteins in the circulatory system is one of the key causes for the aging of organism[6-7]. It is proved by research that the advanced oxidation protein products (AOPP) in the serum damages renal cells, and it is the main pathogenesis of chronic kidney disease. The AOPP in serum can induce the programmed apoptosis of islet β cells[3-8]. The β amyloid hypothesis indicates that the synaptic dysfunction and neuron death resulted from progressive accumulation of toxoprotein induced by unbalance of generation and removal of Aβ protein in tissues are the first causes of AD[9]. The amylin protein not only performs abnormal aggregation in the insular tissues of partial diabetics, but also exists in the plaques of brain tissue, and it is closely related to the progress of diabetes and neurodegenerative diseases[10, 11]. Based on these findings, in some disease models, the Aβ aggregation or formation in the AD animal pattern is blocked by using antibody[12], polypeptide drug[13] or micromolecular drug[14], the formation of neuronal tissue plaques can be reduced, and the animal cognition level is increased. These results show that using drugs to depress the formation and aggregation of these pathogenic proteins or to promote the removal of pathogenic proteins to reduce the accumulation of pathogenic proteins is an important method to prevent or treat these diseases.

Previous research indicates that when the oxidative stress occurs in the cell, the DSS1 (deleted split hand/split foot 1) protein, as a highly conservative small protein in eukaryote, can be covalently modified to oxidized protein under the conditions of enzymatic reaction and ATP consumption, such a modification will mediate the oxidized protein to degrade in the cell[15]. The DSS1 gene knockout leads to cell death; the cells with high expression of DSS1 protein manifest significant resistance to the oxidative stress or antineoplastic-induced cell apoptosis[16]. These results show the vital function of DSS1 protein in the course of removing oxidized protein from cells, and it is the key to the existence of cells.

The related references are described below:
1. Dobson C M (1999) Protein misfolding, evolution and disease. Trends Biochem Sci 24:329-332.
2. Liang M, Wang J, Xie C, Yang Y, Tian J W, Xue Y M, Hou F F (2014) Increased plasma advanced oxidation protein products is an early marker of endothelial dysfunction in type 2 diabetes patients without albuminuria 2. J Diabetes 6(5):417-26.
3. Cao W, Hou F F, Nie J (2014) AOPPs and the progression of kidney disease. Kidney Int Suppl (2011) 4(1):102-106.
4. Sadigh-Eteghad S, Sabermarouf B, Maj di A, Talebi M, Farhoudi M, Mahmoudi J (2015) Amyloid-beta: a crucial factor in Alzheimer's disease. Med Princ Pract 24(1):1-10.
5. Choe Y J, Park S H, Hassemer T, Körner R, Vincenz-Donnelly L, Hayer-Hartl M, Hartl F U (2016) Failure of RQC machinery causes protein aggregation and proteotoxic stress. Nature 531(7593):191-5.
6. Ott C, Grune T (2014) Protein oxidation and proteolytic signalling in aging. Curr Pharm Des 20(18):3040-51.
7. Simm A, Müller B, Nass N, Hofmann B, Bushnaq H, Silber R E, Bartling B (2015) Protein glycation—Between tissue aging and protection. Exp Gerontol 68:71-5.
8. Liang M, Li A, Lou A, Zhang X, Chen Y, Yang L, Li Y, Yang S, Hou F F (2017) Advanced oxidation protein products promote NADPH oxidase-dependent β-cell destruction and dysfunction through the Bcl-2/Bax apoptotic pathway. Lab Invest 24. [Epub ahead of print].
9. Zhao L N, Long H, Mu Y, Chew L Y (2012) The toxicity of amyloid β oligomers. Int J Mol Sci 13(6):7303-27.
10. Fernandez M S (2014) Human IAPP amyloidogenic properties and pancreatic β-cell death. Cell Calcium 56(5):416-27.
11. Lim Y A, Rhein V, Baysang G, Meier F, Poljak A, Raftery M T, Guilhaus M, Ittner L M, Eckert A, Götz J (2010) Abeta and human amylin share a common toxicity pathway via mitochondrial dysfunction. Proteomics 10 (8): 1621-33.
12. Winblad B, Andreasen N, Minthon L, Floesser A, Imbert G, Dumortier T, Maguire R P, Blennow K, Lundmark J, Staufenbiel M, Orgogozo J M, Graf A (2012) Safety, tolerability, and antibody response of active Aβ immunotherapy with CAD106 in patients with Alzheimer's disease: randomised, double-blind, placebo-controlled, first-in-human study. Lancet Neurol 11(7):597-604.
13. Chang L, Cui W, Yang Y, Xu S, Zhou W, Fu H, Hu S, Mak S, Hu J, Wang Q, Ma V P, Choi T C, Ma E D, Tao L, Pang Y, Rowan M J, Anwyl R, Han Y, Wang Q (2015) Protection against β-amyloid-induced synaptic and memory impairments via altering β-amyloid assembly by bis(heptyl)-cognitin. Sci Rep 5:10256.

14. Kim H Y, Kim H V, Jo S, Lee C J, Choi S Y, Kim D J, Kim Y (2015) EPPS rescues hippocampus-dependent cognitive deficits in APP/PS1 mice by disaggregation of amyloid-β oligomers and plaques. Nat Commun 6:8997.
15. Zhang Y, Chang F M, Huang J, Junco J J, Maffi S K, Pridgen H I, Catano G, Dang H, Ding X, Yang F, Kim D J, Slaga T J, He R, Wei S J (2014) DSSylation, a novel protein modification targets proteins induced by oxidative stress, and facilitates their degradation in cells. Protein Cell 5(2):124-40.
16. Rezano A, Kuwahara K, Yamamoto-Ibusuki M, Kitabatake M, Moolthiya P, Phimsen S, Suda T, Tone S, Yamamoto Y, Iwase H, Sakaguchi N (2013) Breast cancers with high DSS1 expression that potentially maintains BRCA2 stability have poor prognosis in the relapse-free survival. BMC Cancer 13:562.

SUMMARY OF THE APPLICATION

In the latest study, we (inventors) have found that there is a new subtype of DSS1 protein in higher primate (anthropoid subfamily) genome, named secretory DSS1 protein (sDSS1). The sDSS1 is the first DSS1 protein subtype discovered, and its sequence, properties and function are highly similar to DSS1. However, it can be secreted into blood and cerebral spinal fluid, its properties are more active, and can form a conjugate with the oxidized protein in serum or buffer solution without energy-consuming enzymatic reaction or combine with Aβ protein and reduce the formation of Aβ oligomer. The sDSS1 protein added to the culture medium can shield the cytotoxicity induced by oxidized protein, Aβ oligomer, amylin oligomer and glycosylated protein to protect cell viability. Therefore, we identify this new type of protein sDSS1 as a promising drug for preventing and treating the diseases induced by oxidized protein, glycosylated protein, Aβ, amylin and other pathogenic proteins with similar features.

The specific technical solution is described below:

A sDSS1 protein is provided, which may have an amino acid sequence of human protein sDSS1 as shown in SEQ ID NO: 1. A protein having the same or similar amino acid sequence as SEQ ID NO: 1 exists in the Anthropoidea animals.

Preferably, the Anthropoidea animals may further be chimpanzee, bonobo, gorilla, orangutan, white-cheeked gibbon, golden snub-nosed monkey, rhesus macaque, olive baboon, *Angola colobus*, sooty mangabey, drill and northern pigtail macaque; wherein *Pan troglodytes* (a chimpanzee) sDSS1 protein has an amino acid as set forth in SEQ ID NO: 5, *Pan paniscus* (a bonobo) sDSS1 protein has an amino acid as set forth in SEQ ID NO: 6, *Gorilla gorilla* (a gorilla) sDSS1 protein has an amino acid as set forth in SEQ ID NO: 7, *Pongo abelii* (an orangutan) sDSS1 protein has an amino acid as set forth in SEQ ID NO: 8, *Nomascus leucogenys* (a white-cheeked gibbon) sDSS1 protein has an amino acid as set forth in SEQ ID NO: 9, *Rhinopithecus roxellana* (a golden snub-nosed monkey) sDSS1 protein has an amino acid as set forth in SEQ ID NO: 10, *Macaca mulatta* (a rhesus macaque) sDSS1 protein has an amino acid as set forth in SEQ ID NO: 11, *Papio anubis* (an olive baboon) sDSS1 protein has an amino acid as set forth in SEQ ID NO: 12, *Colobus angolensis* (a Angola colobus sDSS1 protein has an amino acid as set forth in SEQ ID NO: 13, *Cercocebus atys* (a sooty mangabey) sDSS1 protein has an amino acid as set forth in SEQ ID NO: 14, *Mandrillus leucophaeus* (a drill) sDSS1 protein has an amino acid as set forth in SEQ ID NO: 15, *Macaca nemestrina* (a northern pigtail macaque) sDSS1 protein has an amino acid as set forth in SEQ ID NO: 16.

Preferably, the sDSS1 protein includes a N-terminal amino acid sequence of 58 amino acids and a C-terminal amino acid sequence of 31 amino acids, wherein the human sDSS1 protein has a N-terminal amino acid sequence of 58 amino acids as set forth in SEQ ID NO: 3, the human sDSS1 protein has a C-terminal amino acid sequence of 31 amino acids as set forth in SEQ ID NO: 2; wherein the N-terminal amino acid sequence of the 58 amino acids includes 3 or more amino acid sequences with consecutive acidic amino acids, each of amino acid sequences with consecutive acidic amino acids includes no more than 10 acidic amino acids, any two adjacent amino acid sequences of the amino acid sequences with consecutive acidic amino acids have a spacing of no more than 4 amino acids, and the spacing includes at least one hydrophobic amino acid, a pH value is not higher than 4.5, the N-terminal amino acid sequence of the 58 amino acids includes no less than 10 acidic amino acids; the C-terminal amino acid sequence following position 58 of the N-terminal amino acid sequence of the 58 amino acids are relatively hydrophobic overall, the C-terminal amino acid sequence of the 31 amino acids includes no less than 10 hydrophobic amino acids;

wherein the hydrophobic amino acid is selected from the group consisting of alanine, isoleucine, leucine, valine, cysteine, phenylalanine, methionine, tryptophan, and tyrosine, the neutral amino acid is selected from the group consisting of threonine, glycine, serine, histidine, and glutamine;

the acidic amino acid is selected from the group consisting of glutamic acid, aspartate, proline, and asparaginate; and the basic amino acids is selected from the group consisting of arginine, and lysine.

Preferably, the sDSS1 protein in the Anthropoidea animals includes a C-terminal amino acid sequence of:

$X_1 X_2 X_3 X_4 X_5 X_6 X_7 X_8 X_9 X_{10} X_{11} X_{12} X_{13} X_{14} X_{15} X_{16} X_{17} X_{18} X_{19} X_{20} X_{21} X_{22} X_{23} X_{24} X_{25} X_{26} X_{27} X_{28} X_{29} X_{30} X_{31}$;

$X_1$ is a neutral amino acid; $X_2$ is a hydrophobic amino acid; $X_3$ and $X_4$ are hydrophobic amino acids; $X_5$ is a hydrophobic amino acid; $X_6$ is a hydrophobic amino acid; $X_7$ is a hydrophobic amino acid; $X_8$ is a hydrophobic amino acid; $X_9$ is a hydrophobic amino acid; $X_{10}$ is an acidic amino acid; $X_{11}$ is a neutral amino acid; $X_{12}$ is a hydrophobic amino acid; $X_{13}$ is a hydrophobic amino acid; $X_{14}$ is a neutral amino acid; $X_{15}$ is a hydrophobic amino acid; $X_{16}$ is a hydrophobic amino acid; $X_{17}$ is a hydrophobic amino acid; $X_{18}$ is a hydrophobic amino acid; $X_{19}$ is a basic amino acid; $X_{20}$ is an acidic amino acid; $X_{21}$ is a basic amino acid; $X_{22}$ is a neutral amino acid; $X_{23}$ is a basic amino acid; $X_{24}$ is a hydrophobic amino acid; $X_{25}$ is a hydrophobic amino acid; $X_{26}$ is a neutral amino acid; $X_{27}$ is a hydrophobic amino acid; $X_{28}$ is a hydrophobic amino acid; $X_{29}$ is a hydrophobic amino acid; $X_{30}$ is a hydrophobic amino acid; and $X_{31}$ is a hydrophobic amino acid;

an amino acid sequence having 40% or more homology to the C-terminal amino acid sequence of the 31 amino acids, wherein the amino acid sequence has a same or similar property and function to a C-terminal amino acid sequence of a human sDSS1 protein.

A polypeptide comprising an amino acid sequence constructed based on the N-terminal 58 amino acid sequence and the C-terminal 31 amino acid sequence of the sDSS1 protein as described hereinabove, wherein 1) the polypeptide sequence has a N-terminal having 40% or more homology to the N-terminal amino acid sequence of the 58 amino acids, and the polypeptide sequence has a C-terminal having 40% or more homology to the C-terminal amino acid sequence of the 31 amino acids, a protein encoded by the polypeptide sequence has a same or similar property and function to a human sDSS1 protein; or 2) a N-terminal of the polypeptide sequence is based on a N-terminal amino acid sequence of 58 amino acids of a human sDSS1 protein, or is a sequence having 40% or more homology to the N-terminal amino acid sequence of the 58 amino acids of the human sDSS1 protein, wherein a C-terminal or the N-terminal of the polypeptide is fused with other amino acid sequence, the other amino acid sequence for fusion has an identical or similar property to a C-terminal amino acid sequence of 31 amino acids of the human sDSS1 protein and perform the same or similar functions, a modified protein encoded by the polypeptide sequence performs an identical or similar function to the human sDSS1 protein; or 3) the peptide sequence is constructed by fusing the C-terminal amino acid sequence of the 31 amino acids in the sDSS1 protein, such as is described hereinabove, with other polypeptide sequence.

The fusion protein includes a full sequence or a partial sequence of the sDSS1 protein such as is described hereinabove, and the polypeptide sequence such as is described hereinabove.

Preferably, the fusion protein is a protein complex formed by linking the protein sDSS1 protein, a carrier protein, an antibody or other arbitrary amino acid sequence.

A complex includes a full sequence or a partial sequence of the sDSS1 protein such as is described hereinabove, the polypeptide sequence such as is described hereinabove, or a full sequence or a partial sequence of the fusion protein such as is described hereinabove.

Preferably, the complex is a complex formed by linking the sDSS1 protein to a pharmaceutically acceptable drug carrier.

Preferably, the pharmaceutically acceptable drug carrier includes one or more of a microsphere/capsule, liposome, micro-emulsion, nanoparticle, magnetic particle and gel.

A nucleotide encodes the sDSS1 protein such as is described hereinabove, or the polypeptide such as is described hereinabove.

Preferably, the nucleotide includes DNA and RNA.

A cell expresses the sDSS1 protein such as is described hereinabove or the polypeptide such as is described hereinabove.

Preferably, the cell is a stem cell, a precursor cell or an adult cell of a mammal.

Preferably, the mammal is a human, an orangutan, a monkey, a horse, a cattle, a sheep, a pig, a donkey, a dog, a rabbit, a cat, a rat or a mouse.

Preferably, the cell includes an embryo stem cell, an induced multipotential stem cell or a stem cell derived from a primary culture, a multipotential or monopotential stem cell derived from a mother cell differentiation.

An expression system, wherein a nucleotide sequence encoding the sDSS1 protein such as is described hereinabove or the polypeptide such as is described hereinabove is introduced into an organism, and the sDSS1 protein such as is described hereinabove or the polypeptide such as is described hereinabove is expressed in the organism.

Preferably, the expression system is selected from the group consisting of eukaryotic expression plasmid vector, adenovirus, slow virus, retrovirus, CRISPR/Cas technique and other feasible gene-editing techniques.

Preferably, the organism is a human, an orangutan, a monkey, a horse, a cattle, a sheep, a pig, a donkey, a dog, a rabbit, a cat, a rat, a mouse, a chicken, a duck or a goose.

A drug primarily targets the sDSS1 protein such as is described hereinabove or the polypeptide such as is described hereinabove, wherein the drug can affect an expression level of the sDSS1 protein such as is described hereinabove or the polypeptide such as is described hereinabove in the organism upon administration.

Preferably, the drug is a chemical micromolecular drug, a protein/polypeptide drug, a nucleic acid drug, or a nanodrug.

Preferably, the nucleic acid drug includes one or more of a siRNA, a microRNA, an antisense oligonucleotide, a triple strand DNA and a ribozyme.

A method of producing a protein, includes the following steps:

S1. constructing an expression vector: inserting a nucleotide sequence coding the sDSS1 protein such as is described hereinabove or the polypeptide such as is described hereinabove into a plasmid and introducing the plasmid into bacteria or yeast cell, or inserting the nucleotide sequence coding the sDSS1 protein such as is described hereinabove or the polypeptide such as is described hereinabove into genome of an insect cell or a mammalian cell;

S2. expressing the sDSS1 protein: expanding a culture of the bacteria, yeast cell, insect cell or mammalian cell as modified in S1, and collecting a culture medium or cell lysate containing the sDSS1 protein such as is described hereinabove or the polypeptide such as is described hereinabove;

S3. purifying the sDSS1 protein: coarse filtering and purifying the culture medium or cell lysate obtained in S2 to obtain the sDSS1 protein.

A method of producing a protein, includes using chemical synthesis technique to produce the sDSS1 protein such as is described hereinabove or the polypeptide such as is described hereinabove.

A method of producing a protein, includes using in vitro ribosome expression system to produce the sDSS1 protein such as is described hereinabove or the polypeptide such as is described hereinabove.

A method of diagnosing, preventing or treating disease, includes preparing a diagnostic reagent, a preventive drug, or a therapeutic drug using the sDSS1 protein, polypeptide, fusion protein, complex, nucleotide sequence, cell, expression system, or drug such as is described hereinabove, and administering the diagnostic reagent, preventive drug, or therapeutic drug to a subject in need thereof.

Preferably, the disease is a disease induced by excessive formation or accumulation of pathogenic protein/polypeptide.

Preferably, the pathogenic protein/polypeptide is an oxidized protein product, glycosylated protein product, an amyloid precursor protein and a spliceosome thereof, an islet amyloid polypeptide and a spliceosome thereof, or other pathogenic protein/polypeptides having features similar to an oxidized protein a glycosylated protein, an amyloid protein or an islet amyloid polypeptide.

Preferably, the diagnosing of the disease includes detecting one or more of an expression level of a full or partial sequence of the amino acid sequence, mRNA level and number of gene copies of the sDSS1 protein such as is described hereinabove.

Preferably, the preventing includes one or more of genetic modification, nucleic acid introduction, drug injection/administration, cellular transplantation and tissue transplantation.

Preferably, the treating includes one or more of genetic modification, nucleic acid introduction, drug injection/administration, cellular transplantation and tissue transplantation.

The characteristics and/or beneficial effects of the present application are:

1. The polypeptide sequence of the sDSS1 protein and typical human sDSS1 protein provided by the present application is MSEKKQPVDLGLLEEDDEFEEFPAEDWAGLDEDEDAHVWEDNWDDDNVEDDFSNQLRATVLL MILVCETPYGCYVLHQKGRMCSAFLCC (see SEQ ID NO: 1). According to bioinformatic analysis, the protein is a protein of anthropoid subfamily animals.

2. According to bioinformatic analysis and cell experiment, the 31-amino acid carbon terminal sequence of the sDSS1 protein is a signal peptide and has critical effect on the properties and secretion property of the protein. The C-terminal sequence of the 31 amino acids is TVLLMILVCETPYGCYVLHQKGRMCSAFLCC (see SEQ ID NO: 2).

3. The sDSS1 protein defined in the present application can be combined with oxidized protein, glycosylated protein, Aβ protein and amylin protein and shield the cytotoxicity induced by aggregation of these toxoproteins, so it has important potential in treating the diseases induced by excessive formation or excessive accumulation of these toxoproteins and other pathogenic proteins with similar features.

4. The sDSS1 protein of the present application is produced by fermentation of Escherichia coli. The nucleotide sequence coding the sDSS1 protein is inserted into pET151D plasmid, during sDSS1 expression, the N-terminal is fused with a 6-his tag and a V5 tag for purification and immunoblotting detection. The expression of protein in Escherichia coli is preliminarily purified by using Ni-NTA gel column, and then the SDS-PAGE is used for gel purification. The cut strip of gel containing His-V5-sDSS1 protein is put in a dialysis bag containing transfer buffer, the protein is extracted from the gel under the drive of electric field and collected in the dialysis bag. The protein purified by the SDS polyacrylamide gel electrophoresis analysis can reach the level for bioexperiment.

5. According to molecular experiment, the sDSS1 protein of the present application can be combined with the oxidized protein in serum and the oxidized protein in buffer solution to form conjugates, or combine with Aβ protein to reduce the formation of Aβ oligomer.

6. The cell experiment proves that the sDSS1 protein of the present application can shield the cytotoxicity induced by oxidized protein, glycosylated protein, Aβ oligomer and amylin oligomer in the culture medium effectively, so as to maintain the cell viability.

To sum up, the present application provides a sDSS1 protein, the biological property and activity of sDSS1 protein are proved by the research in bioinformatics, molecular biology and cellular biology. The sDSS1 protein can reduce the cytotoxicity induced by oxidized protein, glycosylated protein, Aβ oligomer and amylin oligomer in culture medium effectively to maintain cell viability. As the sDSS1 protein is a congenital protein of higher primate, it is free of immunoreaction in clinical application. Therefore, the present application provides a candidate drug for preventing and treating the diseases induced by excessive formation or excessive accumulation of oxidized protein, glycosylated protein, Aβ protein, amylin polypeptide and other pathogenic proteins with similar features, and it has important application prospects in biomedicine.

BRIEF DESCRIPTION OF THE DRAWINGS

The present application is further explained by the following attached figures, so as to make the present application clear and complete, but not to limit the scope of protection of the present application.

The sDSS1 gene is a new subtype of DSS1 gene, the comparison between human DSS1 gene cDNA (NM_006304.1, 509 bp) and human sDSS1 gene cDNA (AK309241.1, 1195 bp) shows an overlapping area, the nucleic acid sequence of the overlapping area can encode N-terminal 58 amino acid sequences according to analysis.

Figure 1A:
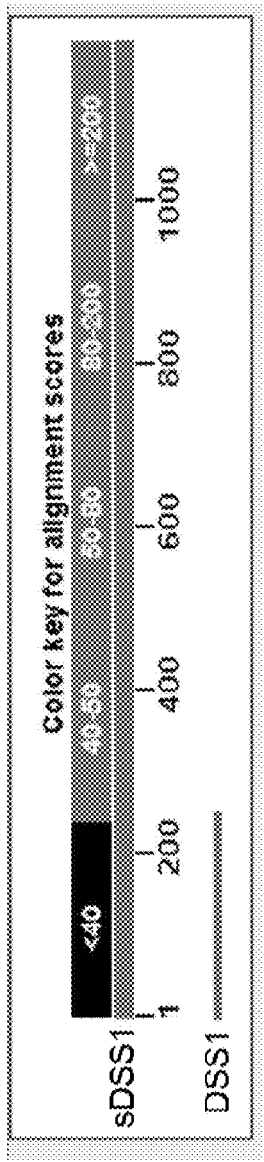
FIG. 1A. illustrates the comparison between human DSS1 gene cDNA and human sDSS1 gene cDNA.
Figure 1B:
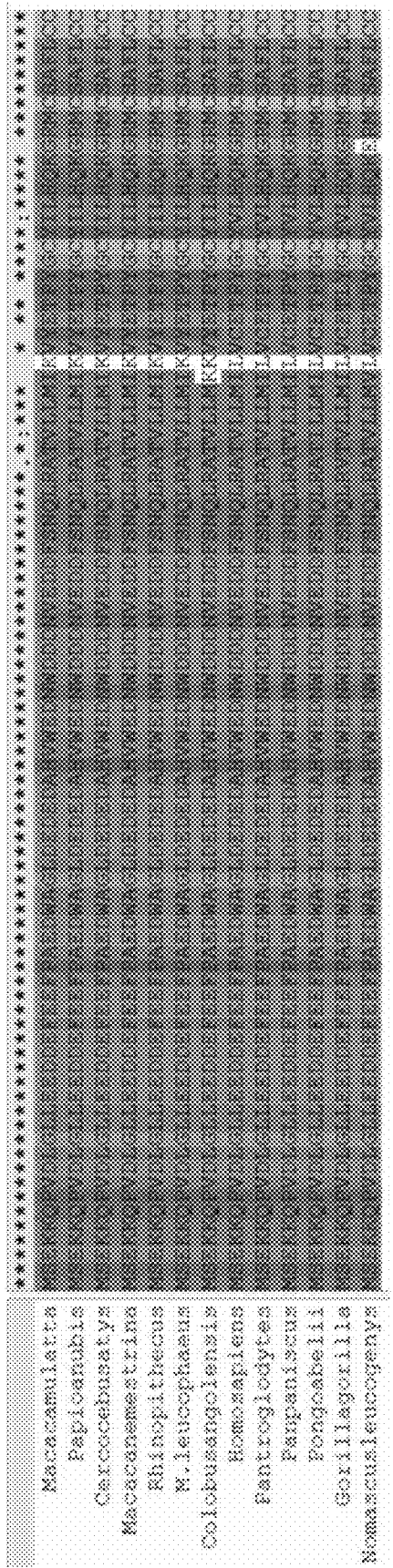

FIG. 1B. illustrates the comparison of The sDSS1 protein amino acid sequences of 13 species of primates.

The sDSS1 protein amino acid sequences of 13 species of primates were compared by using Clustal X2.1 software, the results show that the sDSS1 protein amino acid sequence is highly conservative, N-terminal 58 amino acid sequences are identical, and the C-terminal 31 amino acid sequences have point mutation only at a few sites.

Figure 2A:
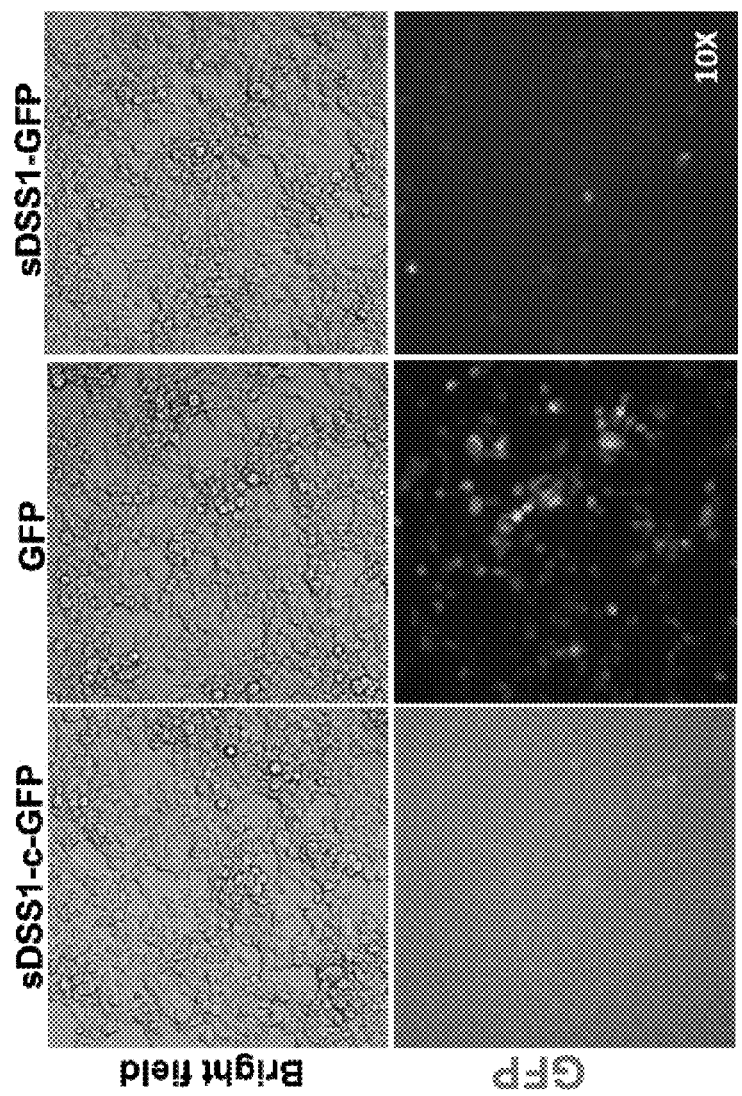

FIG. 2A. illustrates the GFP protein distribution.

In plasmid transfected 293T cell, the GFP protein distribution was observed 24 h later. The green fluorescence in control cell (GFP) was clear and bright, and the background in solution was dim. Obvious green fluorescence signal was observed in the culture solution of sDSS1 and GFP chelated protein (sDSS1-GFP) or sDSS1 protein C-terminal 31 amino acid sequences and GFP chelated protein (sDSS1-c-GFP), and the intracellular fluorescence disperses and the intensity declines, meaning that the GFP protein was taken out of the cell with the sDSS1 protein or sDSS1 protein C-terminal sequence secretion.

Figure 2B:
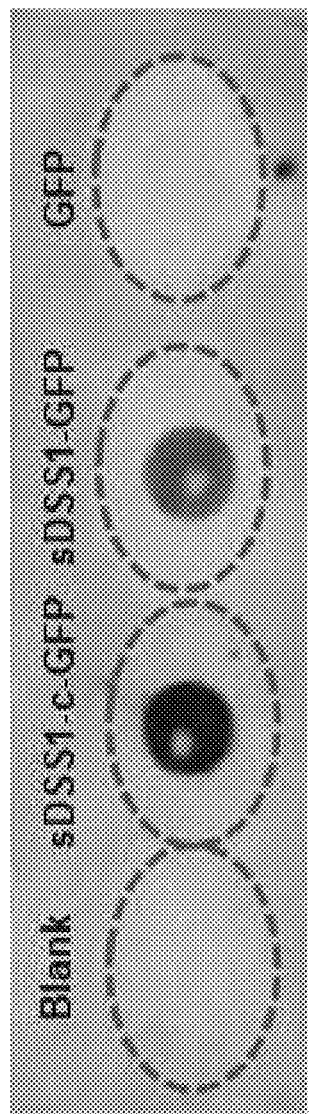

FIG. 2B. illustrates that the sDSS1 protein is a secretory protein.

Point membrane immunoblotting tests for detecting transfected cell culture medium, the results show that the GFP signal was detected in sDSS1-GFP and sDSS1-c-GFP culture media, and there was no obvious signal detected in blank control and GFP control group, proving that the sDSS1 protein is a secretory protein, and C-terminal 31 amino acid sequences are signal peptide.

Figure 3A:
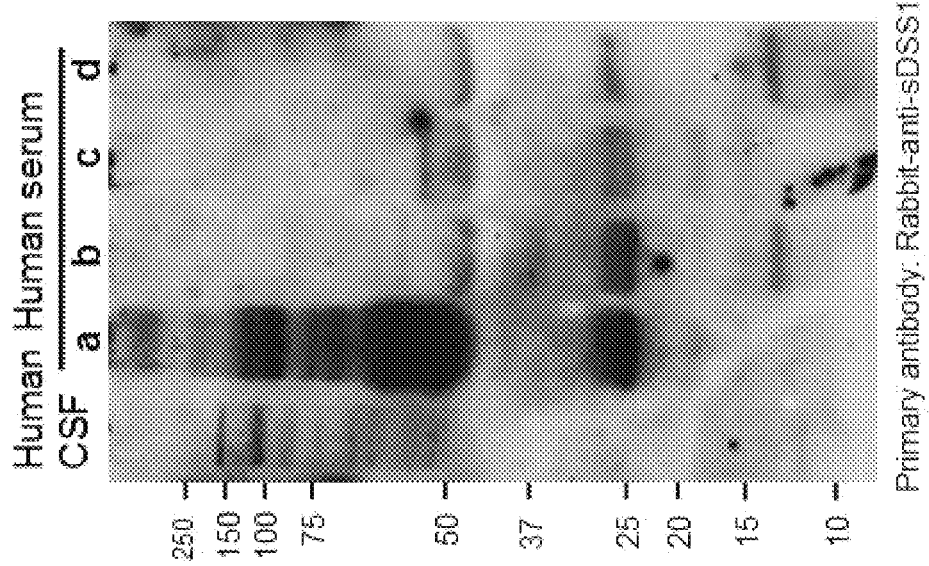

FIG. 3A. illustrates that the sDSS1 signal can be detected in the human serum or human cerebral spinal fluid (CSF) sample.

The sDSS1 signal can be detected in the human serum or human cerebral spinal fluid (CSF) sample by using specific antibody of sDSS1 protein C-terminal polypeptide sequence (antigen sequence: C-terminal 31 amino acid sequences of sDSS1 protein). The Human CSF sample was from senior citizens, the serum sample a was from the blood of a youth after strenuous exercise, the serum samples b, c and d were from the blood of youths in resting state.

Figure 3B:
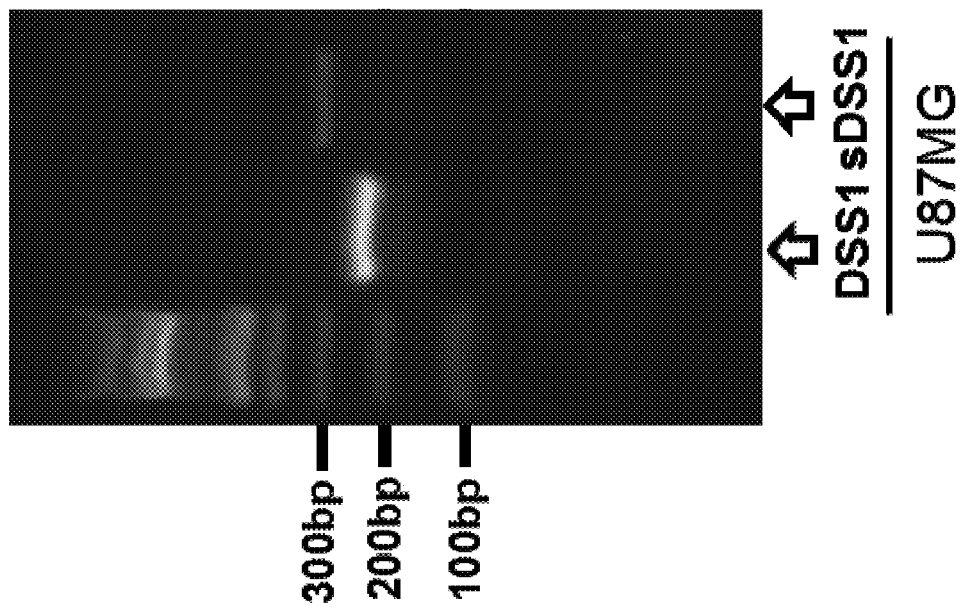

FIG. 3B. illustrates the specific mRNA sequence of sDSS1 gene.

The specific mRNA sequence of sDSS1 gene (amplified product is 293 bp) can be detected in human astrocytomas glioblastoma (U-87 MG) by using PCR, the DSS1 gene is used as control (amplified product is 238 bp).

FIG. 4A-FIG. 4B. illustrates that coomassie brilliant blue staining shows the content of objective protein in the sDSS1 protein production and purification processes.

FIG. 4A. The positive *Escherichia coli* cloning strain was selected to expand culture, the addition of IPTG can induce the expression of sDSS1 protein, the expression level of objective protein in the cell without induction was very low. FIG. 4B. The concentrated lysate after preliminary purification of Ni-NTA gel column and the objective protein content after purification were tested, channel a shows the purified sDSS1 protein, channel b shows the preliminarily purified cell lysis solution.

FIGS. 5A-5D. illustrates that biochemical experiment and cell experiment prove that the sDSS1 protein can combine with oxidized protein and shield the toxicity of oxidized protein.

Figure 5A:
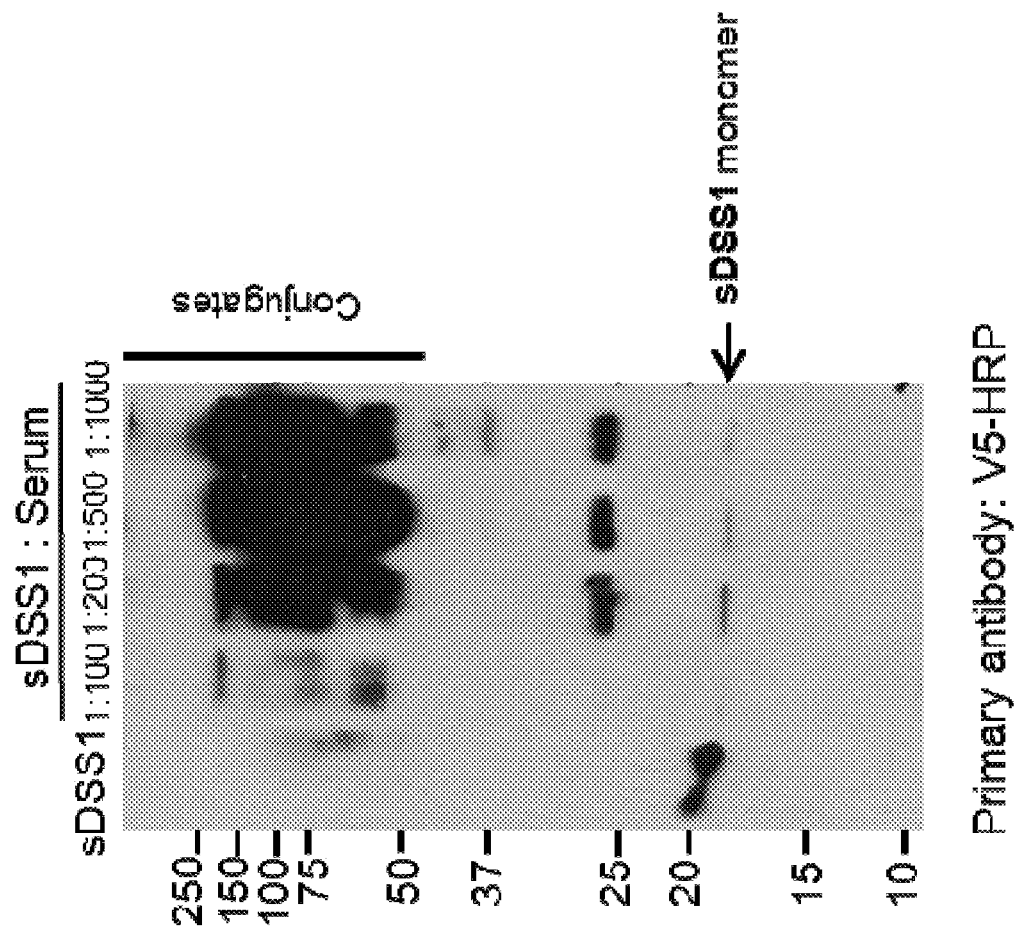
Figure 5B:
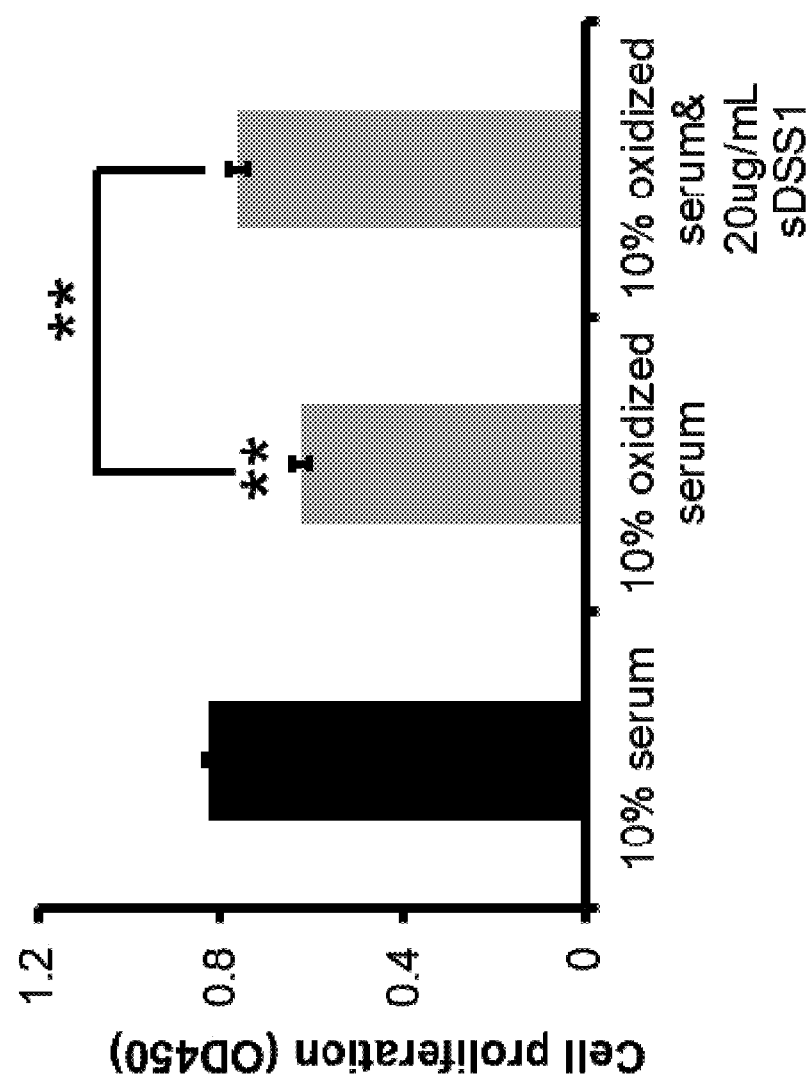
Figure 5C:
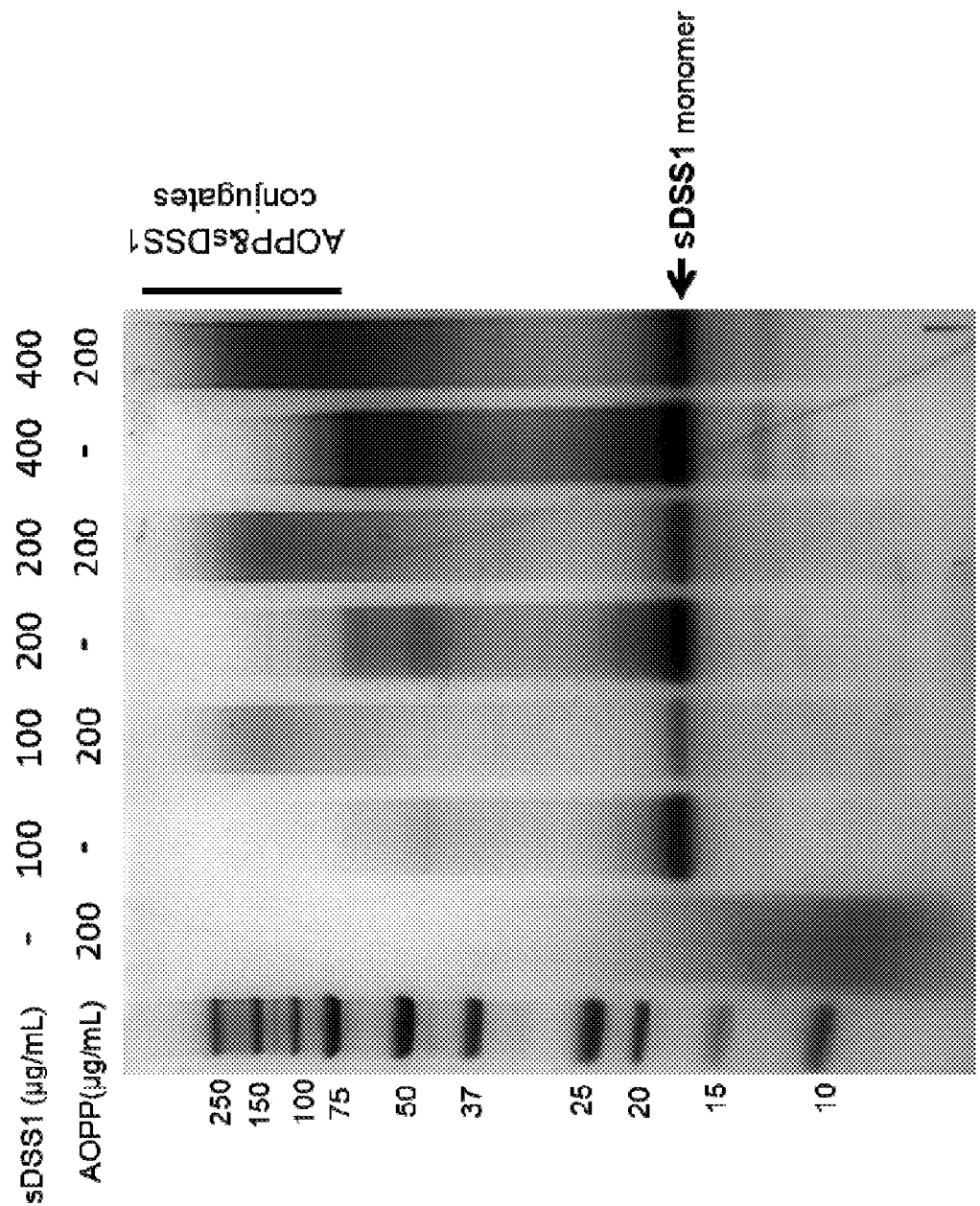
Figure 5D:
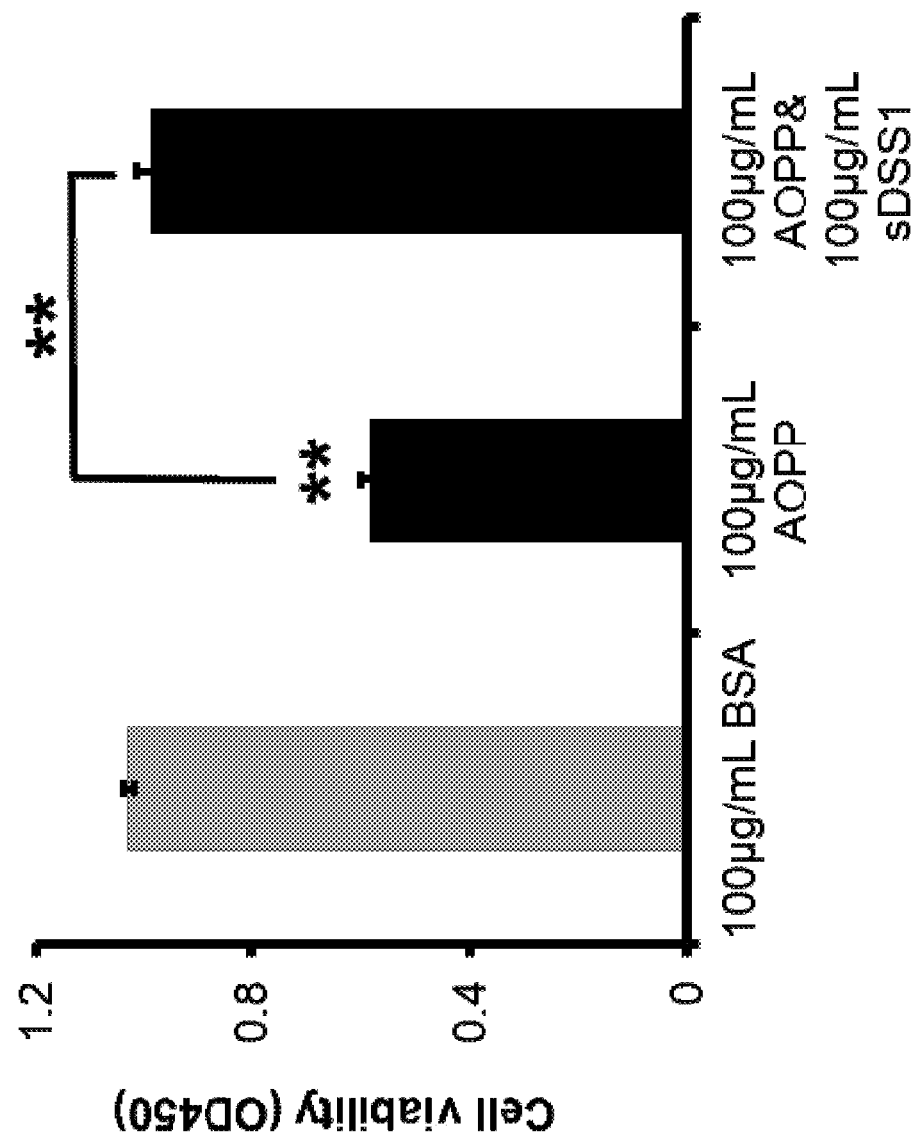

FIG. 5A. The 0.72 μg purified sDSS1 protein was mixed with different proportions of serum protein for incubation, the sDSS1 protein was tested by V5 conjugated protein (V5-HRP), the result shows that the sDSS1 protein and oxidized protein of serum formed macromolecular protein complex. FIG. 5B. The AOPP (200 μg/mL) and the purified sDSS1 proteins at different concentrations were incubated at 4° C. over night, the product was separated by SDS-PAGE, and the Coomassie brilliant blue staining shows that the sDSS1 protein and AOPP can form macromolecular complex, the complex content increases with sDSS1 protein concentration. FIG. 5C. The culture medium is mixed with 10% oxidized serum, the cell proliferation was reduced significantly, the sDSS1 protein in culture medium can shield the cytotoxicity derived from the oxidized serum. FIG. 5D. The culture medium without serum was mixed with 100 μg/mL AOPP protein to reduce the cell viability, the addition of sDSS1 protein at isoconcentration can retrieve cell viability, the 100 μg/mL BSA was used for control group. The data was analyzed by t-test two-tailed test and validated by ANOVE.**, p-value<0.01.

FIGS. 6A-6E. illustrates that the sDSS1 protein reduces the formation of Aβ oligomer, and reduces the cytotoxicity and cell apoptosis induced by Aβ oligomer.

Figure 6A:
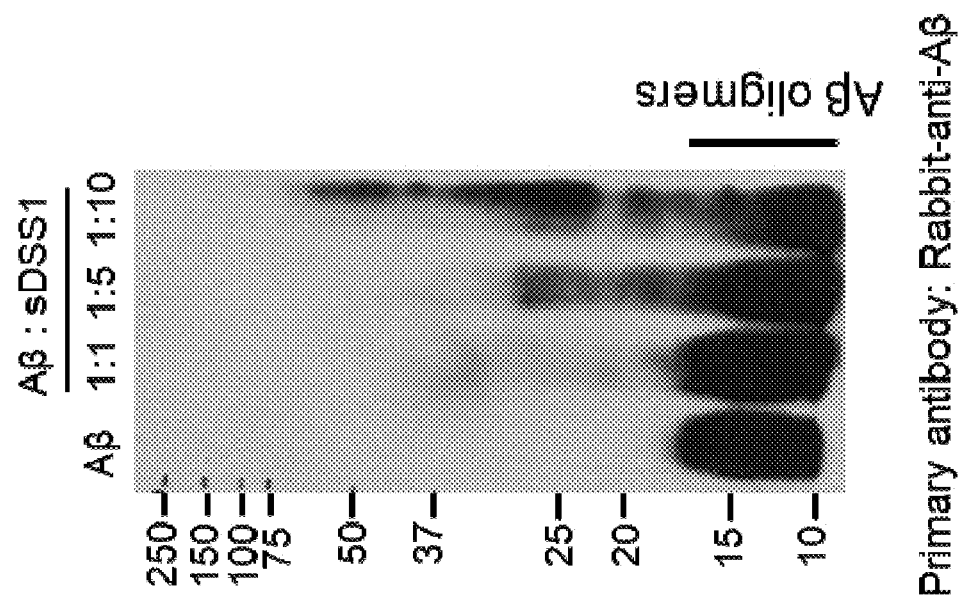
Figure 6B:
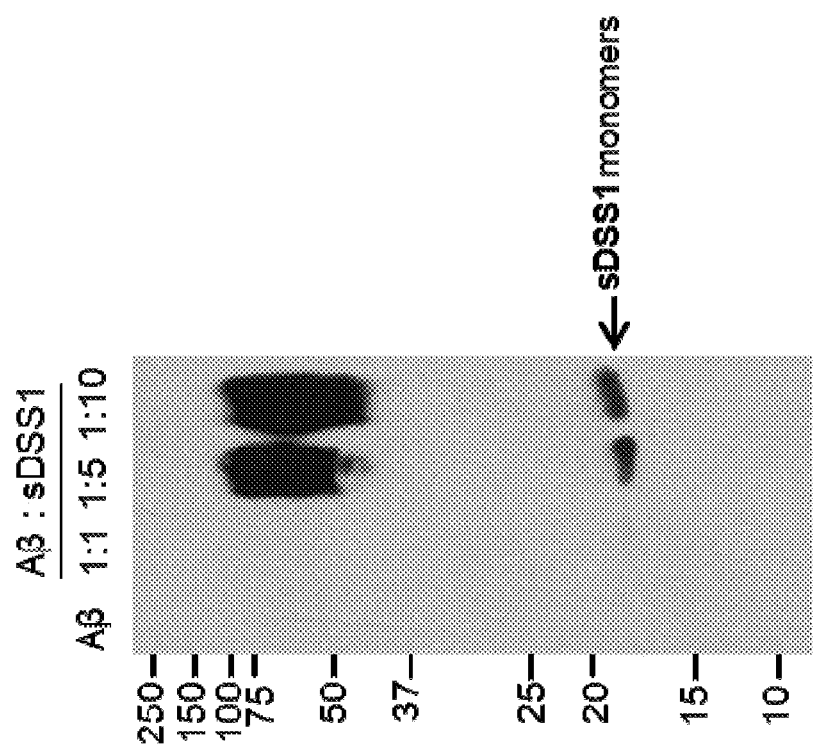
Figure 6C:
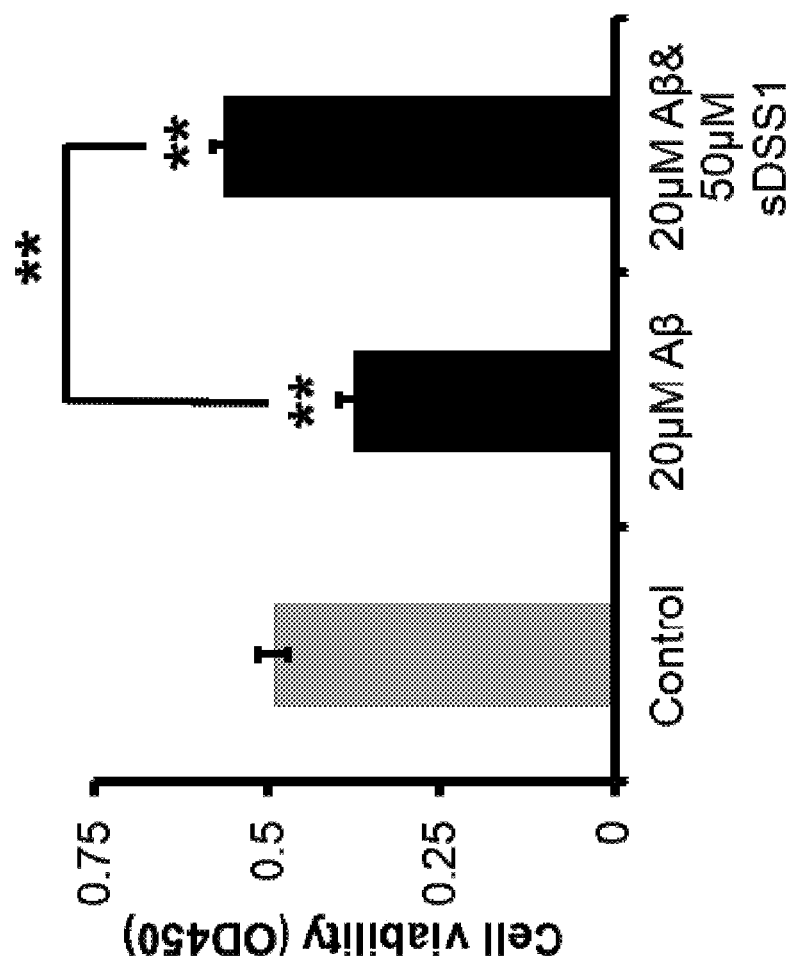
Figure 6D:
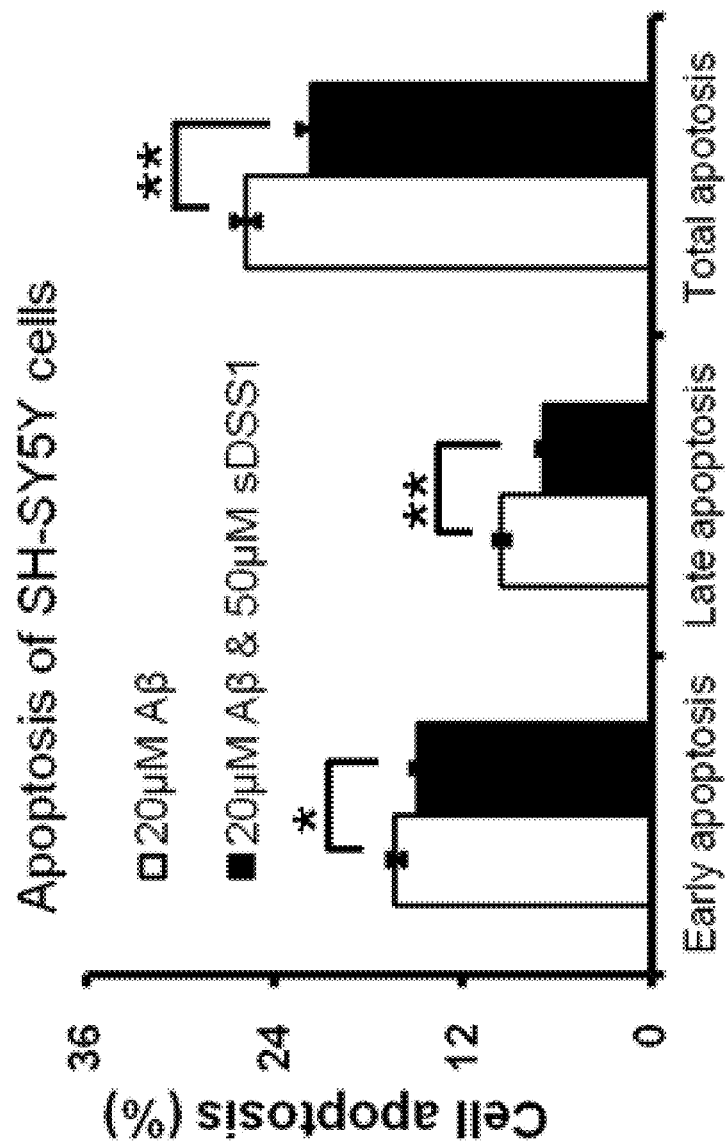
Figure 6E:
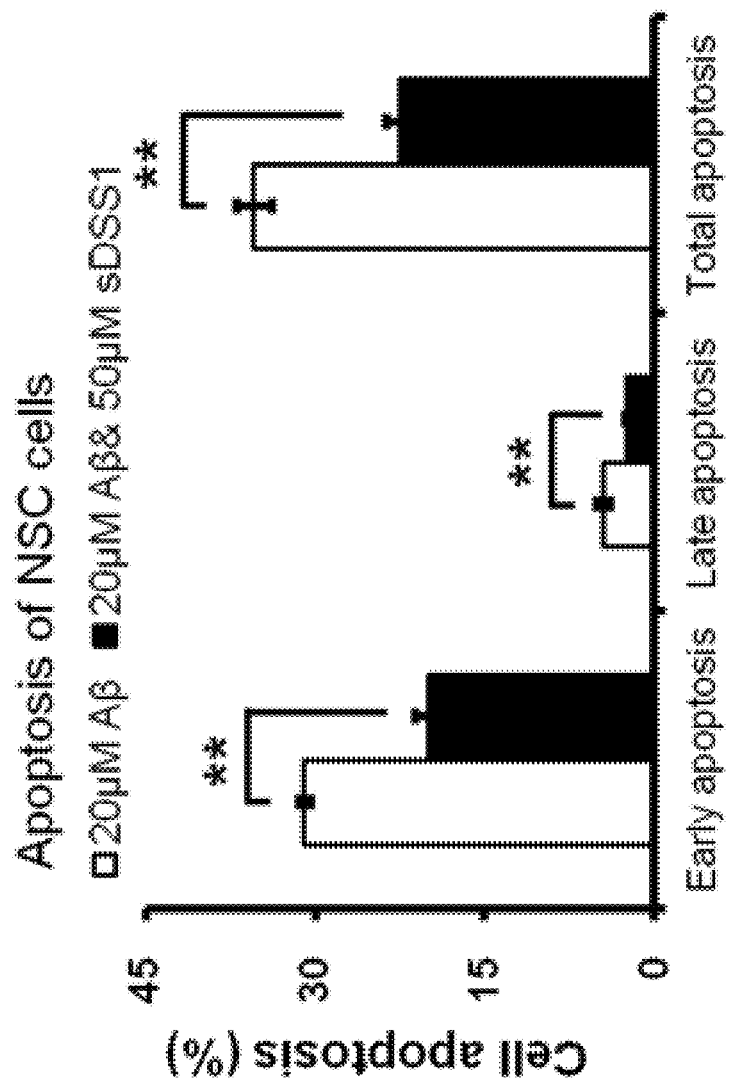

FIG. 6A. Different proportions of sDSS1 protein were mixed with 10 μg Aβ protein before incubation, according to Aβ antibody test, the sDSS1 protein and Aβ formed covalently conjugated high molecular weight protein complex, such a conjugation can reduce the formation of Aβ oligomer with cytotoxicity. FIG. 6B. V5 sDSS1 protein was tested by conjugated protein (V5-HRP), the result shows that the sDSS1 protein and Aβ formed a protein complex. FIG. 6C. The addition of Aβ oligomer to the culture medium induced cytotoxicity, the cell viability was degraded, the sDSS1 protein can shield the cytotoxicity induced by Aβ oligomer completely. FIG. 6D. The cell apoptosis experiment shows that the sDSS1 protein added to the culture medium reduced the early apoptosis and late apoptosis of SH-SY5Y cells induced by Aβ oligomer significantly, so as to reduce the effect of toxoprotein on cells. FIG. 6E. The sDSS1 protein can shield the toxicity of Aβ oligomer for mouse nerve stem cells (NSCs). The data was analyzed by t-test two-tailed test and validated by ANOVE. **, p-value<0.01.

Figure 7:
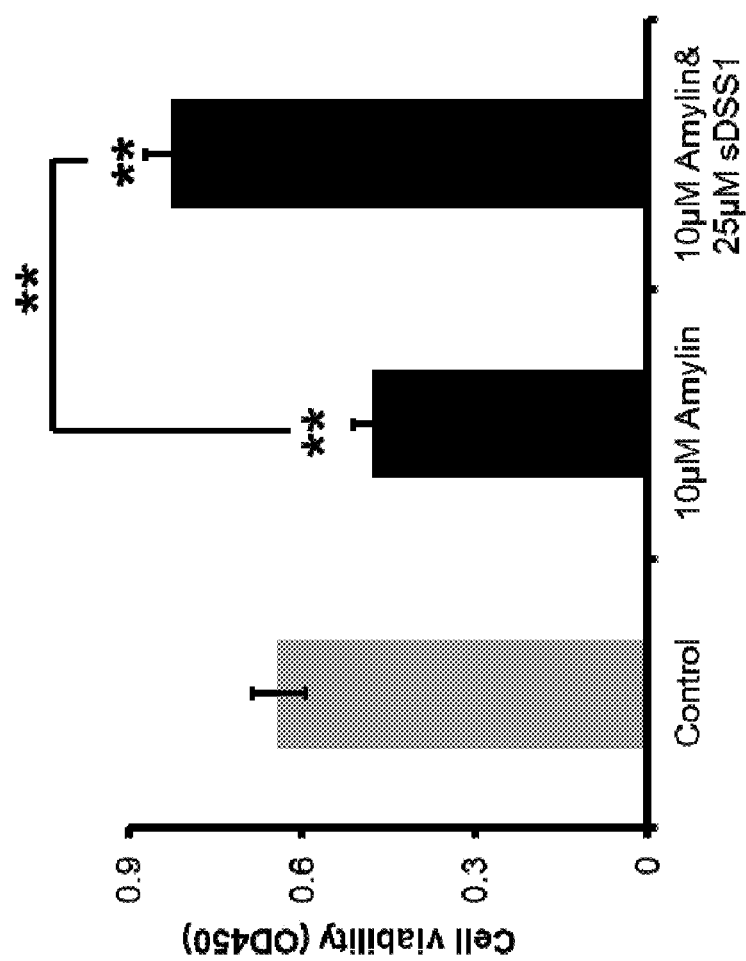

FIG. 7. illustrates that the addition of sDSS1 protein can retrieve the cell viability, promoting the cell survival.

The amylin oligomer added to the culture medium induces cytotoxicity and reduces cell viability, the addition of sDSS1 protein can retrieve the cell viability, promoting the cell survival. The data was analyzed by t-test two-tailed test and validated by ANOVE. **, p-value<0.01.

Figure 8:
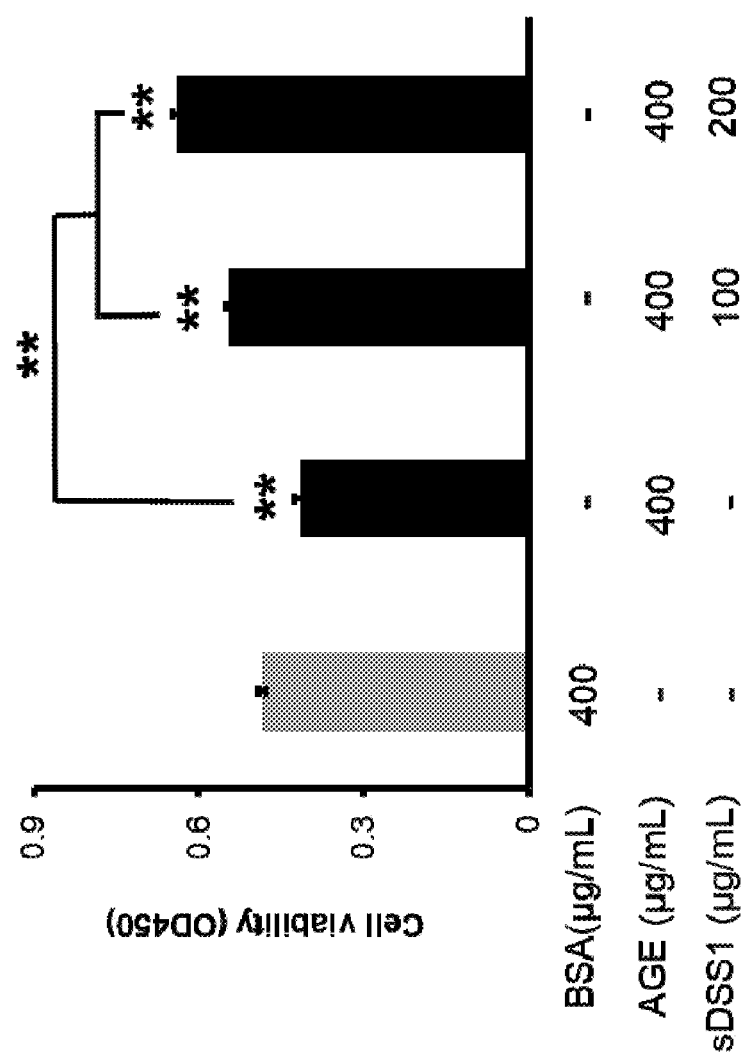

FIG. 8. illustrates that the cell viability decline can be retrieved by sDSS1 protein.

The cell viability decline induced by 400 μg/mL glycosylated protein can be retrieved by sDSS1 protein, the retrieving effect increased with the sDSS1 protein concentration (100 μg/mL to 200 μg/mL). The 400 μg/mL BSA protein was used for control group. The data was analyzed by t-test two-tailed test and validated by ANOVE.**, p-value<0.01.

Figure 9A:
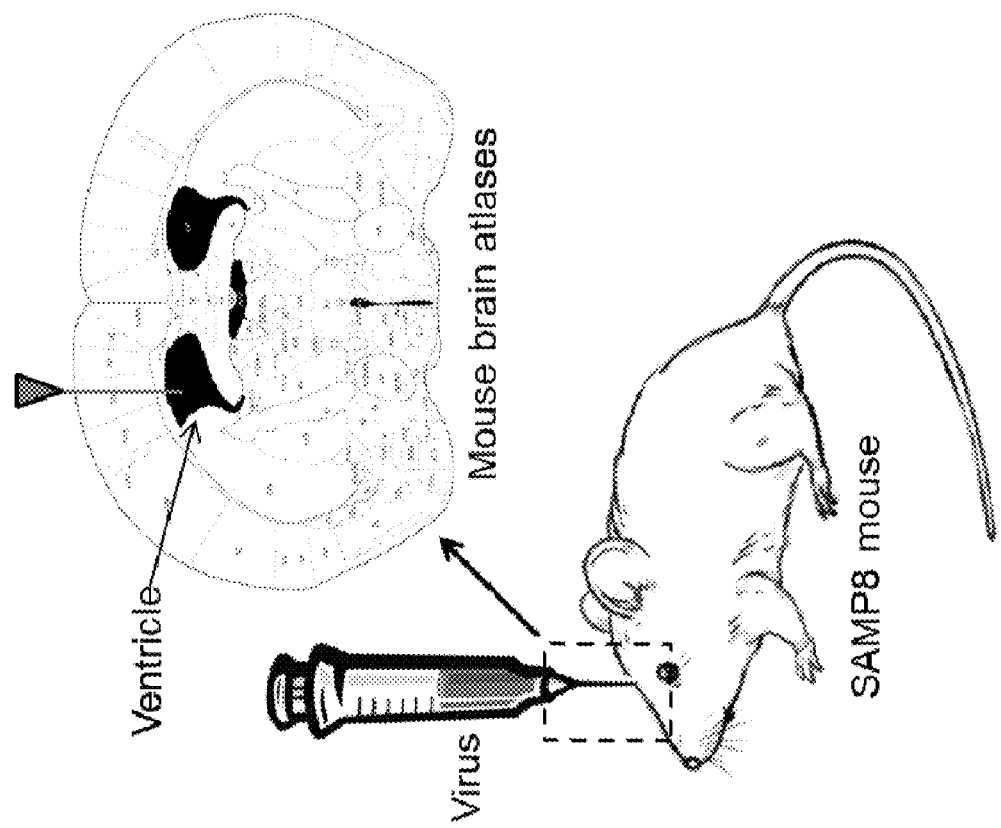

FIG. 9A. illustrates that Operating method of injecting virus into the lateral ventricle of SAMP8 mouse and virus injection site.

Figure 9B:
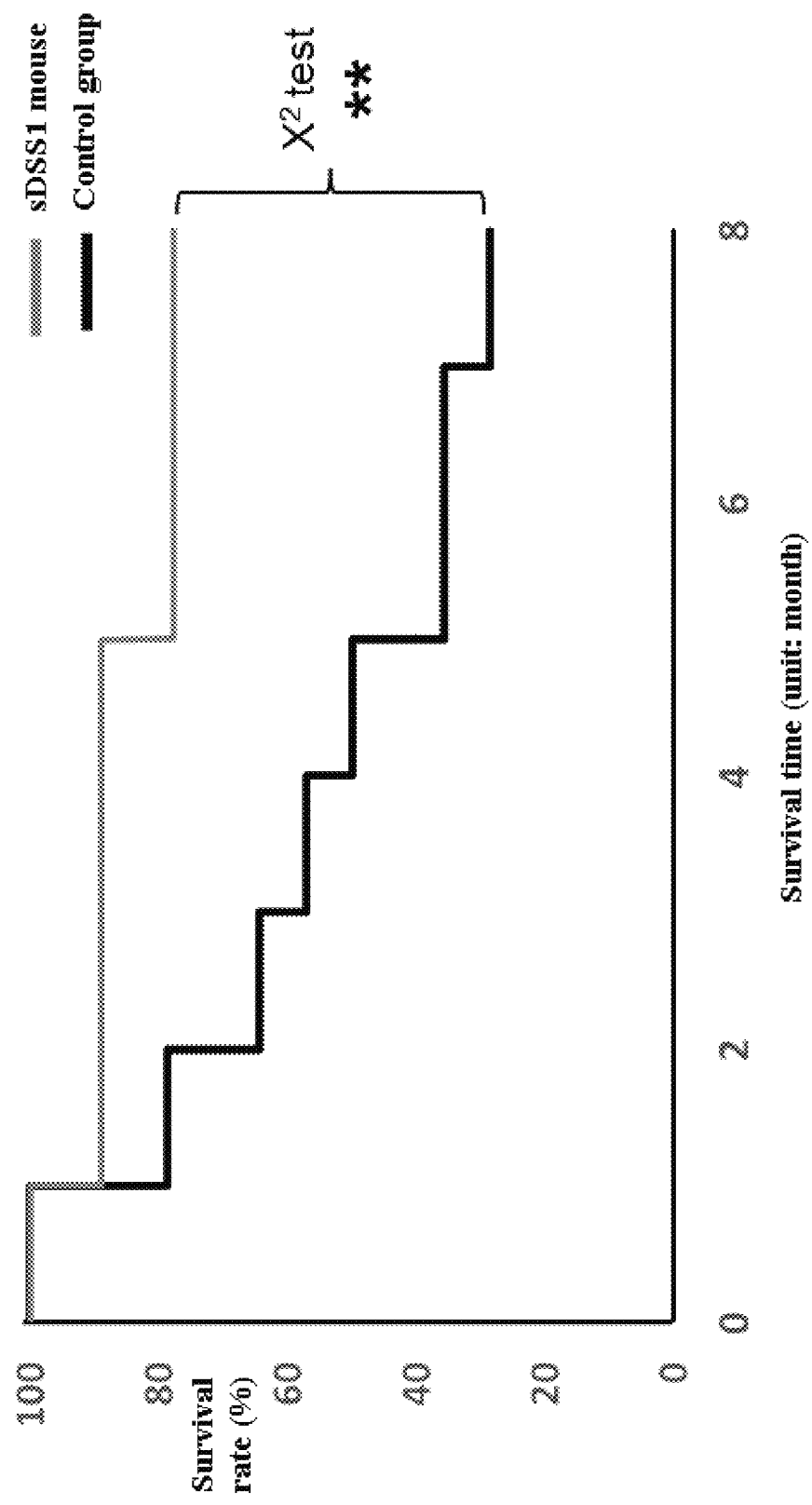

FIG. 9B. illustrates that the survival rate after operation of the mouse injected with adenovirus expressing sDSS1 protein was apparently higher than that of control mouse.

The adenovirus was injected into the lateral ventricle of a 5 months old senescence-accelerated mouse SAMP8 mouse (1 μL virus into right and left brains respectively), the animal survival was observed continuously. The result shows that the survival rate after operation of the mouse injected with adenovirus expressing sDSS1 protein was apparently higher than that of control mouse (expressing GFP protein). The data was analyzed by ANOVE.**, p-value<0.01.

DETAILED DESCRIPTION OF THE EMBODIMENTS

The preferred solutions of the present application are described and validated with examples in the following text, not to limit the scope of the present application. All scope of the present application are subject to the scope of the Claims.

The experimental methods for the following cases are conventional experimental methods unless otherwise specified.

In the following embodiments, the sDSS1 protein was produced in-house and its purity reached the level for bioexperiment, the other materials and reagents were commercially available.

Example 1 sDSS1 Protein is a Secretory Protein from Primate

Bioinformatic Analysis Tool:

National Center of Biotechnology Information (NCBI) genome database; Nucleotide blast tool (NCBI); Align sequences nucleotide blast tool (NCBI), Translate tool (SIB Bioinformatics Resource Portal); Clustal X2.1: Multiple Sequence Alignment (EMBL-EBI); SecretomeP 2.0 (CBS prediction service); WoLF PSORT II.

Bioexperimental Method:

1. Cell culture, the 293T cells were bought from American type culture collection (ATCC), the cells were cultured in the cell culture medium containing 90% basal medium (Dulbecco's modified eagle medium, DMEM) (Life technology C #12500062) and 10% Fetal bovine serum (FBS) (Gibco C #10100-147), cultured in cell incubator (temperature 37° C., humidity 95%, CO2 concentration 5%), subcultured once every two days.

2. Cell transfection, the 293T cells were inoculated in a 6-well plate as per $3 \times 10^5$ per well, mixed with 1.5 mL cell culture medium, the plasmid was transfected when the cells have been adhering to the wall for 12 hours. The eukaryotic expression plasmid pCMV-C-Flag was used, the inserted nucleic acid sequence expressing sDSS1 protein was expressed as SEQ ID NO: 17. 2500 ng of the plasmid was diluted and mixed with 750 uL Opti-MEM® Medium (Life technology C #31985062) uniformly, 10 μL transfection reagent Lip2000 (Invitrogen C #12566014) was diluted and mixed with 750 μL Opti-MEM® Medium uniformly, the diluted plasmid solution was instilled into the diluted transfection reagent drop by drop, mixed uniformly and incubated at normal temperature for 5 minutes. The cell culture medium was blotted from the 6-well plate, the cells were cleaned with PBS, and then the incubated transfection working fluid was applied. The cells were cultured in the incubator continuously, the fluorescent protein expression of the cells 2 was observed during 24 to 48 hours.

3. Western blotting, the PVDF membrane was activated by methanol and dried, the control culture medium and different transfection cell culture media were dripped onto the membrane. When the membrane was dried, the PVDF membrane completed 1% BSA sealing, primary antibody (Rabbit-anti-GFP) (Cell signal technology C #2956) incubation, secondary antibody (Goat-anti-rabbit HRP antibody) (Zsbio, ZDR-5403) incubation in turn. The membrane was cleaned with PBST three times, developed by luminescent liquid (Zsbio, ZLI-9017) and the bands were exposed by X-ray film.

Result Analysis:

In the bioinformatic analysis of shfm1 gene in human genome, it was found that the gene has multiple transcripts (see shfm1 gene information in NCBI database, http://www.ncbi.nlm.nih.gov/gene/7979). Besides an mRNA sequence of jointly coded DSS1 protein sequence (NM_006304.1, 509 bp), there is a longer mRNA sequence (AK309241.1, 1195 bp). The short mRNA sequence and long mRNA sequence only have 256 bp repeat sequence (FIG. 1A). According to nucleic acid sequence analysis, it can be seen from the Translate tool that the repeat sequence can encode DSS1 protein N-terminal 58 amino acid sequences. The long mRNA sequence coded for 89 amino acids. According to the alignment of polypeptide sequences, the long mRNA encoded polypeptide sequence and DSS1 polypeptide sequence have the overlapping area of N-terminal 58 amino acids, and the variation area of 31 amino acids. This new polypeptide was named secretory DSS1 protein (sDSS1), the polypeptide sequences are expressed as follows:

```
DSS1 (Homo sapiens):
MSEKKQPVDLGLLEEDDEFEEFPAEDWAGLDEDEDAHVWEDNWDDDNVE

DDFSNQLRAELEKHGYKMETS (see SEQ ID NO: 4)

s-DSS1 (Homo sapiens):
MSEKKQPVDLGLLEEDDEFEEFPAEDWAGLDEDEDAHVWEDNWDDDNVE

DDFSNQLRATVLLMILVCETPYGCYVLHQKGRMCSAFLCC
(see SEQ ID NO: 1)
```

According to the screening of the sequenced primate genome and other animal pattern genomes in NCBI database, only the genome of Anthropoidea animals has similar long mRNA sequence and polypeptide sequence similar to human sDSS1 protein, as shown in Table 1. The polypeptide sequence alignment results show that the sDSS1 protein sequence is highly conservative, the N-terminal 59 amino acid sequences are identical, the other C-terminal amino acid sequences have a little point mutation (FIG. 1B).

TABLE 1

| Primate | Species | Amino acid sequence |
|---|---|---|
| Haplorrhini | Homo sapiens | MSEKKQPVDLGLLEEDDEFEEFPAEDWAGLDEDEDAHVWEDNWDDD NVEDDFSNQLRATVLLMILVCETPYGCYVLHQKGRMCSAFLCC (see SEQ ID NO: 1) |
| | Pan troglodytes | MSEKKQPVDLGLLEEDDEFEEFPAEDWAGLDEDEDAHVWEDNWDDD NVEDDFSNQLRATVLLMILVCETPYGCYVLHQKGRMCSAFLCC (see SEQ ID NO: 5) |
| | Pan paniscus) | MSEKKQPVDLGLLEEDDEFEEFPAEDWAGLDEDEDAHVWEDNWDDD NVEDDFSNQLRATVLLMILVCETPYGCYVLHQKGRMCSAFLCC (see SEQ ID NO: 6) |
| | Gorilla gorilla) | MSEKKQPVDLGLLEEDDEFEEFPAEDWAGLDEDEDAHVWEDNWDDD NVEDDFSNQLRVTVLLMILVCETLYGCYVLHQKGRMCSAFLCC (see SEQ ID NO: 7) |
| | Pongo abelii | MSEKKQPVDLGLLEEDDEFEEFPAEDWAGLDEDEDAHVWEDNWDDD NVEDDFSNQLRATILLMILVCETPYGCYVLHQKGRMCSAFLCC (see SEQ ID NO: 8) |
| | Nomascus leucogenys | MSEKKQPVDLGLLEEDDEFEEFPAEDWAGLDEDEDAHVWEDNWDDD NVEDDFSNQLRATVLLMVLVCETPYGCYVLHQKERMCSAFLCC (see SEQ ID NO: 9) |
| | Rhinopithecus roxellana | MSEKKQPVDLGLLEEDDEFEEFPAEDWAGLDEDEDAHVWEDNWDDD NVEDDFSNQLRATVLLMIKVYETPYGCYILHQKGRMCSAFLCC (see SEQ ID NO: 10) |
| | Macaca mulatta | MSEKKQPVDLGLLEEDDEFEEFPAEDWAGLDEDEDAHVWEDNWDDD NVEDDFSNQLRATVLLMIKVYETPYGCYILHQKGRMCSAFLCC (see SEQ ID NO: 11) |
| | Papio anubis | MSEKKQPVDLGLLEEDDEFEEFPAEDWAGLDEDEDAHVWEDNWDDD NVEDDFSNQLRATVLLMIKVYETPYGCYILHQKGRMCSAFLCC (see SEQ ID NO: 12) |

TABLE 1-continued

| Primate Species | Amino acid sequence |
|---|---|
| Angola colobus | MSEKKQPVDLGLLEEDDEFEEFPAEDWAGLDEDEDAHVWEDNWDDD<br>NVEDDFSNQLRATVLLMKKVYETPYGCYILHQKGRMCSAFLCC<br>(see SEQ ID NO: 13) |
| Sooty mangabey | MSEKKQPVDLGLLEEDDEFEEFPAEDWAGLDEDEDAHVWEDNWDDD<br>NVEDDFSNQLRATVLLMIKVYETPYGCYILHQKGRMCSAFLCC<br>(see SEQ ID NO: 14) |
| Mandrillus leucophaeus | MSEKKQPVDLGLLEEDDEFEEFPAEDWAGLDEDEDAHVWEDNWDDD<br>NVEDDFSNQLRATVLLMIKVYETPYGCYILHQKGRMCSAFLCC<br>(see SEQ ID NO: 15) |
| Macaca nemestrina | MSEKKQPVDLGLLEEDDEFEEFPAEDWAGLDEDEDAHVWEDNWDDD<br>NVEDDFSNQLRATVLLMIKVYETPYGCYILHQKGRMCSAFLCC<br>(see SEQ ID NO: 16) |

The sDSS1 protein amino acid sequence was analyzed by using two kinds of secretory protein analysis and prediction software, which are Wolf PSORT and SecretomeP 2.0. The prediction results show that the sDSS1 protein is located outside the cells, similar to multiple identified secretory proteins, it is estimated as a secretory protein (Table 2). According to the analysis result of Wolf PSORT software, the signal peptide cleavage site of sDSS1 protein is located between amino acids positions 58-59.

TABLE 2

| Species Name | SecretomeP 2.0<br>(Recommended threshold for secreted protein: 0.6) | WoLF PSORT<br>(Numbers of similar secreted proteins) | Predicted protein location |
|---|---|---|---|
| Homo sapiens | 0.85 | 28 | Extracellular |
| Pan troglodytes | 0.85 | 28 | Extracellular |
| Pan paniscus | 0.85 | 28 | Extracellular |
| Nomascus leucogenys | 0.85 | 27 | Extracellular |
| Gorilla gorilla | 0.752 | 23 | Extracellular |
| Pongo abelii | 0.86 | 27 | Extracellular |
| Rhinopithecus roxellana | 0.836 | 29 | Extracellular |
| Macaca mulatta | 0.836 | 29 | Extracellular |
| Angola colobus | 0.823 | 28 | Extracellular |
| sooty mangabey | 0.836 | 29 | Extracellular |
| M. leucophaeus | 0.836 | 29 | Extracellular |
| Macaca nemestrina | 0.836 | 29 | Extracellular |
| Papio anubis | 0.836 | 29 | Extracellular |

According to the bioinformatic analysis results, the complete sequence or C-terminal 31 amino acid sequences (31 amino acid sequences after amino acid position 58) of the protein are connected to green fluorescent protein (GFP) and expressed in 293T cells (sDSS1-GFP, sDSS1-c-GFP). The results show that the solution had green fluorescence, the background emitted light, and the fluorescence in the cells was dim. There was no fluorescence in the control group (GFP) solution, the background was very dark, the fluorescence in the cells was clear and bright (FIG. 2A). The cell culture medium was tested by point membrane immunoblotting, the GFP signal was detected in the cell culture media of sDSS1-GFP and sDSS1-c-GFP groups, but the signal was not detected in the control group (GFP) (FIG. 2B). To sum up these results, the sDSS1 protein is a sort of secretory protein, it can be synthesized in the cells and secreted out of the cells, the C-terminal 31 amino acid sequences of sDSS1 protein perform the function of signal peptide.

Example 2 sDSS1 Protein is a Naturally-Occurring Protein

1. Human serum and CSF sample treatment. Fresh human whole blood was collected, kept still at room temperature for 10-20 minutes, 3500 g centrifuged for 30 minutes, the supernatant was human serum. The serum was mixed with 100 mM mercaptoethanol uniformly and treated by boiling water bath for 10 minutes, 12000 g high speed centrifuged for 10 minutes after cooling, the supernatant and ⅕ of 5×loading buffer solution by volume were mixed. The fresh CSF was obtained from hospital and placed in ice box for transportation, treated on the day. The fresh CSF was mixed with 5×loading buffer directly and made into samples directly for loading.

2. Western blotting, 15 μL prepared loading sample was put in the loading well, the protein was separated with 4-12% prefabricated gel (Life technology C #NP0321BOX) and moved to PVDF membrane. The membrane was subjected to primary antibody (Rabbit-anti-sDSS1) (antigen sequence: C-terminal 31 amino acid sequences of sDSS1 protein) incubation, PBST solution cleaning three times; and secondary antibody (Goat-anti-rabbit HRP antibody) incubation. It was cleaned with PBST three times, developed by luminescent liquid and the bands were displayed by X-ray film.

3. Cell culture, the human glioma cells (U87-MG cells) were bought from ATCC, the cells were cultured in complete cell culture medium containing 90% basal medium DMEM and 10% FBS, cultured in cell incubator (temperature 37° C., humidity 95%, CO2 concentration 5%), subcultured once every two days.

4. PCR experiment, the U87-MG cells were collected and lysed rapidly, the total RNA was extracted from cell lysis solution by using a total RNA extraction kit (QIAGEN, 51304), the RNA sample was treated with 1 U/μL DNase I at room temperature for 15 minutes to remove residual genome DNA. The obtained RNA sample was all converted and synthesized into cDNA by using a cDNA synthesis kit (TransGen Biotech, AT301) and used as template sample for subsequent PCR experiment. 20 μL reaction system was used in the PCR reaction, including 100 μL, PCR premixed reagent (PCRTaq Mixture) (Omega bio-tek, TQ2200), 0.5 μL cDNA template (3.5 μg/mL), 0.5 μL primer, 9 μL ultrapure water, mixed uniformly before PCR reaction. DSS1 cDNA primers: forward primer: GCA-GACAGTCGAGATGTCAGAG, reverse primer: TTCTTCTGGATGCTATGAAGTCTCC; sDSS1 cDNA primers: forward primer: GCA-GACAGTCGAGATGTCAGAG, reverse primer: TGAT-GATCTGTTAACAGCAGAGG. PCR reaction procedure: 94° C. 10 minutes, cyclic reaction 40 times: including 94° C. 10 s, 62° C. 20 s, 72° C. 20 s, 72° C. 10 minutes after the circulation is finished, stored at 4° C. and the DNA content in PCR product was tested by 3% sepharose [0.05% SYBR Green Stain (Thermo Fisher, 4472903)] electrophoresis.

Result Analysis:

The signal of sDSS1 protein can be detected in CSF or serum by using the specific antibody of sDSS1. The serum samples derived from different individuals manifest different signal modes, the sDSS1 signal in the serum of the individual after exercise was apparently higher than that of the individual in resting state (FIG. 3A). The mRNA signal of sDSS1 gene can be detected in U87-MG cells, the gene sequencing result of PCR amplified product was identical to the sequence of database (FIG. 3B). These results show that the sDSS1 protein is a sort of protein, existing in CSF and serum.

Example 3

Small-Amount Preparation of sDSS1 Protein

Experimental Method

1. SDSS1 protein preparation: the nucleotide segment of total gene synthesis coded human sDSS1 protein (see SEQ ID NO: 17) was inserted into the back of Hisx6-V5 tag in pET151D. The plasmid was transferred to the expression strain BL21 (DE3). The Escherichia coli was fused with expression Hisx6-V5-sDSS1 protein, the Ni-NTA gel column was used for preliminary purification, and then the SDS-PAGE was used for gel purification. The cut strip containing His-V5-sDSS1 protein was put in the bag filter with transfer buffer. The protein was removed from the gel under the drive of electric field and collected in the bag filter. The protein was concentrated to about 500 dialyzed in PBS solution at 4° C. four times, 200 ml each time.

2. SDS polyacrylamide gel electrophoresis, the purified sDSS1 protein or bacterial lysis solution protein was mixed with 5× loading buffer solution, treated by boiling water bath for 10 minutes, 12000 g high speed centrifuged for 10 minutes, the supernatant was extracted for analysis. The protein was separated by 4-12% prefabricated gel, the gel was stained for 1 hour using Coomassie brilliant blue staining solution, and decolored by destainer at room temperature over night. When the decolorization was completed, the bands on the gel were observed and photographed.

Result Analysis:

The positive cloned Escherichia coli strain was selected, the culture was expanded, the bacterial cells were stimulated by IPTG to express objective protein at the beginning of logarithmic phase of bacterial growth. The bacteria were lysed, the objective protein expression level was tested. The result shows after the IPTG stimulation, the sDSS1 protein expression level of bacterial cells was upgraded significantly. The protein bands were obvious in the gel image (FIG. 4A). After the bacterial lysis solution was preliminarily purified by Ni-NTA gel column, the objective protein in concentrate was concentrated greatly (channel b), the impure protein content decreased, very pure sDSS1 protein could be obtained by further purification (channel a)(FIG. 4B), applicable to subsequent bioexperiment. The purified sDSS1 protein was quantified by BCA protein, the final concentration was 0.72 mg/ml, stored at 4° C. for future use.

Example 4 sDSS1 Protein Reacts with Oxidized Protein and Shields Cytotoxicity of Oxidized Protein Experimental Method 1. Reaction between oxidized serum and sDSS1 protein, 3500 g of fresh blood was centrifuged for 30 minutes, the upper serum was extracted for subsequent experiment. The 10 μL sDSS1 protein solution (0.72 mg/mL) was mixed with 10, 20, 50 and 100 μL oxidized serums respectively, the mass ratios of sDSS1 to serum protein were about 1:100, 1:200, 1:500 and 1:1000, mixed with 20 μM Fenton reagent ($FeSO_4$ and $H_2O_2$ were mixed as per mass ratio of 1:1), incubated in a dark place at 4° C. over night. On the next day, the reacting His-V5-sDSS1 was separated by using 10 μL Ni-NTA beads. The reactant liquor was mixed with the beads at 4° C. for 2 hours, the magnetic separation device adsorbed the beads on the tube wall, the liquid was removed, 1 ml PBST was applied, the tube was removed from the magnetic separation device, after repeated oscillation cleaning, the magnetic separation device adsorbed the beads, the PBST was sucked away, and the above steps were repeated four times. Finally, the protein was eluted with 50 μL TBS containing 50 mM EDTA, the eluent was mixed with isometric 2×SDS solution, treated at 100° C. for 10 minutes, 12000 g centrifuged for 10 minutes, the supernatant was extracted for test. The supernatant was mixed with 5× loading buffer solution, heated at 100° C. for 10 minutes, the prepared sample was used for western blotting.

2. Preparation of oxidized FBS and AOPP, 10 mL FBS was mixed with 10 mM NaC10 and treated for 1 hour, the oxidized serum was dialyzed continuously in PBS solution using 3000 Da bag filter for 24 hours, the solution was changed at intervals of 8 hours during dialysis, the treated serum solution was mixed with 1 mM vitamin C (Vc) to remove the participant oxidizer completely. The protein concentration was tested by BCA protein quantification. The content of oxidized protein was tested by using two methods, the dityrosine value in the oxidized serum measured by chloramine-T was 75.31 μM/mg protein (untreated serum was 15.05 μmol/mg protein), the carbonyl content detected by dinitrophenylhydrazine was 16.33 nmol/mg protein (untreated serum was 13.68 nmol/mg protein).

The 10 mg serum albumin was treated with 160 mM NaC10 for 1 hour, the oxidized protein was dialyzed continuously in PBS solution using 3000 Da bag filter for 24 hours, the solution was changed at intervals of 8 hours during dialysis. The protein concentration of the treated AOPP was determined by BCA protein quantification. The dityrosine value of AOPP sample measured by chloramine-T was 54.21 μmol/mg protein (untreated BSA was 14.55 μmol/mg protein), the carbonyl content measured by dinitrophenylhydrazine was 1042.57 nmol/mg protein (untreated BSA was 10.26 nmol/mg protein).

3. Reaction between AOPP and sDSS1 protein, the 150 μL reaction system was mixed with 30 μg AOPP protein (200 μg/mL), and mixed with 15 μg (100 μg/mL), 30 μg (200 μg/mL) and 60 μg (400 μg/mL) sDSS1 protein respectively, the excess volume was supplemented by aseptic PBS solution. The solution was stirred uniformly and reacted at 4° C. over night. The sample after reaction was mixed with 5× loading buffer solution, heated at 100° C. for 10 minutes, the treated sample was separated by SDS-PAGE and the bands were displayed by Coomassie brilliant blue staining.

4. Western blotting, the protein mixture after reaction was mixed with 5× loading buffer, treated by boiling water bath for 10 minutes for western blotting analysis. The specific method was the same as described above. The antibody was V5-HRP antibody (1:5000 diluted).

5. Cell line culture, the human neuroblastoma cells (SH-SYSY) were grown in the basal medium DMEM with 10% FBS; the cells were subcultured once every two days.

6. Cell viability test, in order to test the effect of sDSS1 protein on the cytotoxicity of oxidized serum, the SH-SYSY cells were inoculated to a 96-well plate as per $10^4$ cells per well, 2000, complete medium. 12 hours later, the complete medium was changed to DMEM without serum containing 0.5% BSA 200 μL per well. After 24 hours of treatment, the DMEM solution was changed to 10% oxidized serum and 10% oxidized serum containing 20 μg/mL sDSS1 protein as culture medium, 200 μL per well. After 48 hours of treatment, the old culture medium was removed from the 96-well plate, 100 μL diluted CCK-8 working fluid (1:20 diluted) (DOJINDO, CK04) was put in each well to test the changes in cell viability. The group with BSA at isoconcentration was the control group.

In order to test the protective effect of sDSS1 protein on the cytotoxicity induced by AOPP, the SH-SYSY cells were inoculated to the 96-well plate as per $2\times10^4$ cells per well, after 12 hours of adhesion, the culture medium was changed to culture medium without serum containing 0.5% BSA. After 24 hours of treatment, it was changed to culture medium without serum containing 100 μg/mL AOPP protein, and the treatment group was provided with 100 μg/mL sDSS1 protein, 200 μL per well. After 48 hours of treatment of 96-well plate, the changes in cell viability were tested by using CCK-8 kit.

Result Analysis:

The serum contained a lot of proteins, mainly being serum albumin. Under the effect of Fenton reagent, the proteins in serum were oxidized, the oxidation products reacted with sDSS1 to foam complexes. In control group, the sDSS1 protein monomer had no obvious protein aggregation. In the experimental group, the co-incubation with serum led to the formation of lots of high molecular weight protein complexes, these complexes cannot be separated by SDS-PAGE (FIG. 5A). The result shows that the sDSS1 protein can combine with the oxidized protein in serum. In the cytotoxicity experiment, compared with control serum, the addition of 10% oxidized protein could depress cell proliferation and cell viability obviously, and 20 μg/mL sDSS1 protein in the culture medium could retrieve the cytotoxicity of oxidized protein (FIG. 5B).

The sDSS1 was mixed with AOPP, the sDSS1 and AOPP were combined to form complexes, these complexes cannot be separated by SDS-PAGE. The number of complexes increased apparently with the sDSS1 protein concentration in the reaction system (FIG. 5C). In the cell experiment, the AOPP had significant cytotoxicity for cells, reducing the cell viability, and the sDSS1 at isoconcentration could shield the cytotoxicity of AOPP completely (FIG. 5D). To sum up the results, the sDSS1 can protect the cells from the cytotoxicity of oxidized serum or AOPP.

In addition, to sum up the reaction between sDSS1 protein and oxidized protein, two proteins can combine with the oxidized protein tightly, this binding force can resist high concentration of SDS, which seems to be covalent interaction. The difference is that the combination process of DSS1 and oxidized protein needs the assistance of an ATP enzyme [Zhang et al, 2014]. Our evidence shows that the tight coupling of sDSS1 and oxidized protein is free of ATP, the ATP enzyme is not required. According to the amino acid sequences of DSS1 and sDSS1, the sequences of amino acid positions 1 to 58 of the two proteins are identical, and the sequence of amino acid positions 59 to 70 of DSS1 are completely different from the sequence of amino acid positions 59 to 89 of sDSS1. The tight coupling of DSS1 and sDSS1 with oxidized protein is supposed to be derived from the shared amino acid sequences, i.e. the sequence of the first 58 amino acids. The difference in characteristic between sDSS1 and DSS1, which is the characteristic that the tight coupling with oxidized protein is free of ATP enzyme mediation, should be derived from the unique amino acid sequence of sDSS1, i.e. C-terminal amino acid sequence of positions 59 to 89. Altogether, the tight coupling with oxidized protein without ATP enzyme mediation of sDSS1 is derived from the organic combination of the sequences of the first 58 amino acids and the last 31 amino acids.

Example 5 sDSS1 Protein Reduces the Formation of Aβ Oligomer and Reduces the Cytotoxicity of Aβ Oligomer Experimental Method 1. Cell line culture, the human neuroblastoma cells (SH-SY5Y) were grown in the basal medium DMEM with 10% FBS; the cells were subcultured once every two days.

2. Neural stem cell culture, the neural stem cells (NSCs) were from P2 mouse brain tissue, the NSCs of primary suspension culture were used for toxicity test after two subcultures, the NSCs were cultured in the stem cell culture medium, including 88% DMEM/F12 basal medium (Gibco, C #12500-062), 10% Proliferation supplementary additive (Stem cell technology, C #05701), 2% BSA (Sigma, C #V900933), 10 ng/mL Heparin (Sigma, C #H3149), 10 ng/mL bFGF (Roche, C #11104616001), 20 ng/mL EGF (BD Bioscience, C #354010).

3. Reaction between Aβ and sDSS1 proteins, the Aβ protein (Human, 1-42) freeze-dried powder was supplied from Suzhou Qiangyao Biotechnology Co., Ltd. 2 mg Aβ freeze-dried powder was dissolved by 20 μL DMSO, diluted with PBS to 2 mg/mL, stored at −20° C. The reaction system was provided with 300 μL PBS solution the 10 μg Aβ and sDSS1 proteins were mixed as per molar mass ratios 1:1, 1:5 and 1:10, and then incubated at 4° C. over night. The incubated reactant was mixed with 5× loading buffer solution, treated at 100° C. for 10 minutes for western blotting analysis.

4. Aβ protein pretreatment, the Aβ stock solution was diluted with basal medium (pH7.2) to 1000 μg/mL, the Aβ diluent was incubated at 4° C. for 24 hours to form oligomer for cell experiment. The Aβ concentration in subsequent experiment was always labeled according to the protein concentration before incubation.

5. Western blotting, the treated reactant was separated by SDS-PAGE for western blotting analysis, the specific method was the same as described above. The antibodies used were V5-HRP antibody (1:5000 diluted), Aβ antibody (Cell signal technology, 9888), secondary antibody (Goat-anti-rabbit HRP antibody).

6. Cell viability test, the SH-SY5Y cells were inoculated to the 96-well plate as per 2×10$^4$ cells per well, after 12 hours of adhesion, the old culture medium was changed to culture medium without serum containing 0.5% BSA, after 24 hours of treatment, the old culture medium was changed to DMEM solution containing Aβ or Aβ and sDSS1 proteins. After 48 hours of treatment of cells, the cell viability level was tested by CCK-8 kit.

7. Cell apoptosis test, the cell apoptosis test kit was bought from DOJINDO chemical technology (Shanghai) corp. (AD10). The SH-SY5Y cells were inoculated to the 6-well plate as per 3×10$^5$ cells per well, after 12 hours of adhesion, the old culture medium was changed to DMEM solution without serum containing 0.5% BSA. After 24 hours of treatment, it was changed to solution containing Aβ or Aβ and sDSS1 proteins. After 48 hours of treatment, the cell apoptosis level was tested by apoptosis kit. All of the solution and cells were collected, the supernatant was removed by centrifugation. The cells were resuspended in the 400 μL staining buffer solution provided by the apoptosis kit, 185 μL cell suspension was extracted for subsequent test. The cell suspension was mixed with 5 μL Annexin V staining solution uniformly, the cells were incubated at 37° C. for 10 minutes. It was mixed with 10 μL PI staining solution uniformly, the cell apoptosis level was tested by flow cytometer.

The NSCs were firstly adhered and cultured in the 6-well plate, the plate was treated with 0.025% Laminin for at least two hours and cleaned with aseptic PBS 6 times for future use. The NSCs were made into unicells and inoculated to 6-well plate as per 3×10$^5$ per well, the cells were adhered for 24 h for subsequent experiment.

Result Analysis

The Aβ protein had obvious aggregation after incubation, there were protein aggregates of different sizes formed within 10-20 KD. According to previous reports, these Aβ oligomers were the main source of the Aβ induced cytotoxicity. After co-incubation of sDSS1 protein and Aβ, the sDSS1 protein and Aβ protein aggregated to form high molecular weight complex (molecular weight higher than 20 KD), the oligomers formed withtin 10-20 KD were reduced obviously (FIG. 6A). As the sDSS1 protein concentration increased, the formation of Aβ oligomer was depressed apparently. According to the sDSS1 protein signal detection, the complex was formed by the reaction between sDSS1 protein and Aβ (FIG. 6B), and it could not be separated by SDS-PAGE.

The shielding effect of sDSS1 protein on the Aβ induced cytotoxicity was tested. In the cell viability test, the cell viability declined significantly after the pretreated Aβ oligomer was applied. When the culture medium was mixed with sDSS1 protein, the SH-SY5Y cell viability was recovered significantly and the cell viability was higher than control group (FIG. 6C). In the cell apoptosis test, the addition of Aβ oligomer to the culture medium induced the apoptosis of SH-SY5Y cells or NSCs. The addition of sDSS1 protein to the culture medium can reduce the early apoptosis and late apoptosis levels of cells significantly (FIG. 6D, FIG. 6E). According to the results, the sDSS1 protein can combine with Aβ protein to reduce the Aβ oligomer formation, so as to mitigate the cytotoxicity induced by Aβ protein.

Example 6 sDSS1 Protein Reduces Cytotoxicity of Amylin Oligomer

Experimental Method

1. Cell line culture, the human neuroblastoma cells (SH-SY5Y) were grown in the basal medium DMEM with 10% FBS; the cells were subcultured once every two days.

2. Amylin protein pretreatment, the amylin protein (Human) freeze-dried powder was supplied from Suzhou Qiangyao Biotechnology Corp. The 2 mg amylin freeze-dried powder was dissolved to 2 mg/mL in 10 mM sodium acetate solution (pH5.5), stored at −20° C. The amylin stock solution was diluted to 1 mg/mL with basal medium (pH7.2). The amylin diluent was incubated at 4° C. for 48 hours to form oligomer for cell experiment. The amylin concentration in subsequent experiment was always labeled according to the protein concentration before incubation.

3. Cell viability test, the SH-SY5Y cells were inoculated to 96-well plate as per 2×10$^4$ cells per well, after 12 hours of adhesion, the old culture medium was changed to culture medium without serum containing 0.5% BSA. After 24 hours of treatment, the old culture medium was removed and the DMEM solution containing amylin or amylin and sDSS1 proteins was applied. After 48 hours of treatment of cells, the cell viability level was tested by CCK-8 kit.

Result Analysis

The addition of 10 μM inbubated amylin protein to the cell culture medium can induce significant cytotoxicity, and the addition of sDSS1 protein can shield the cytotoxicity induced by amylin oligomer, the cell viability was even higher than control group (FIG. 7), meaning the sDSS1 protein can shield the cytotoxicity of amylin protein effectively.

Example 7 sDSS1 Protein Reduces Cytotoxicity of Glycosylated Protein Experimental Method

1. Cell line culture, the human neuroblastoma cells (SH-SY5Y) were grown in the basal medium DMEM with 10% FBS; the cells were subcultured once every two days.

2. Glycosylated protein preparation, 10 mg/mL serum albumin and 2.5M ribose were mixed and incubated at 37° C. for 7 days, and then dialyzed in PBS using 3000 Da bag filter for 24 hours, the solution was changed at intervals of 8 hours. The completed glycosylated protein was quantified by BCA, the sample was stored at −80° C. for future use.

3. Cell viability test, the SH-SY5Y cells were inoculated to 96-well plate as per 2×10$^4$ cells per well, after 12 hours of adhesion, the old culture medium was changed to culture medium without serum containing 0.5% BSA. After 24 hours of treatment, the old culture medium was removed and the DMEM solution containing glycosylated protein or glycosylated protein and sDSS1 proteins at different concentrations was applied, the group with BSA at isoconcentration was used for control. After 48 hours of treatment of cells, the cell viability level was tested by CCK-8 kit.

Result Analysis

The addition of 400 μg/mL glycosylated protein to the cell culture medium can induce significant cytotoxicity, and the addition of sDSS1 protein can reduce the cytotoxicity induced by glycosylated protein. As the sDSS1 protein concentration increased, the cell viability was even higher than control group (FIG. 8), meaning the sDSS1 protein can shield the cytotoxicity of glycosylated protein effectively.

Example 8 sDSS1 Protein Prolongs Postoperative Survival Time of Senescence-Accelerated Mouse SAMP Experimental Method 1. Animal feeding, the senescence-accelerated SAMP8 mice (5 months old, male) were bought from Beijing Vital River Laboratory Animal Technology Co., Ltd., the animals were fed at the clean laboratory animal breeding center of Southern Model Organism Center. The animals were provided with sufficient aseptic water and standard mouse breeding feed, 12 h/12 h dark-and-bright alternate illumination, the bedding and cage were changed monthly, the animal survival was observed daily.

2. Adenovirus synthesis, the nucleic acid sequence (see SEQ ID NO: 17) of adenovirus expressing sDSS1 protein was provided by us (inventors), the adenovirus construction and synthesis were completed by Cyagen (Guangzhou) Biotechnology Co., Ltd. The adenovirus promoter and transcription region sequence composition: pAV[Exp]-UBC>EGFP:T2A:ORF_363 bp, including ubiquitin protein promoter sequence. According to determination, the virus titer was larger than $10^{10}$ PFU/mL. According to the validation by infecting U87-MG cells and mouse neuroblastoma cells (N2a), the adenovirus can infect cells and express sDSS1 protein efficiently. The adenovirus expressing GFP protein (pAV[Exp]-UBC>EGFP) was used as control.

3. Stereotactic injection, the senescence-accelerated SAMP8 mouse (6 months old, male) was anaesthetized by intraperitoneal injection with 20% urethane (dissolved in normal saline, impurities and bacteria removed by 0.22 μm filter) as per 800 mg/kg body weight. When the mouse was anaesthetized, it was fixed to the mouse stereotaxic apparatus (Stoelting, 51500), the cranial bone was kept horizontal. The head skin was incised to expose the cranial bone, the bregma was taken as the starting coordinate to locate the lateral ventricle region (0.58 mm, 1.25 mm, 1.75 mm). The marking point was perforated by dental drill. 2 μL of virus liquid was sucked by the microinjector (Hamilton 600-2.5 μL, syringe needle diameter 0.2 mm), the lateral ventricle region was relocated according to the same coordinate values. The needle was inserted into the lateral ventricle region quickly according to the specified coordinate values, the virus liquid was injected slowly at 200 nL/min on average, for a total amount of 1000 nL. After the injection was done, each time the needle was lifted for 0.25 mm, it was waited for 3 minutes until the needle was drawn out of the brain tissue completely. The lateral ventricle region on the opposite side was relocated, the needle insertion, injection and needle lifting were completed, 1 μL virus liquid was injected. For the mouse after injection, the cranial bone and peripheral tissues were wiped with 100 U/mL ampicillin/streptomycin, and the skin was sutured. The abdominal cavity of the mouse was injected with 150 μL antibiotics, and the mouse was put in the cage with abdomen up until the mouse was awake.

Result Analysis

The schematic diagram indicates the basic operation of injecting virus into the mouse's lateral ventricle and the adenovirus injection site (FIG. 9A). Wherein there were two batches of mice injected with adenovirus expressing sDSS1, 10 mice in total; there were two batches of mice injected with adenovirus expressing GFP, 14 mice in total. Within 1 month after the injection of adenovirus, three mice of the control group died, and one mouse of the experimental group died. Within 8 months, the mice of the control group died successively, whereas only one mouse of the experimental group died (FIG. 9B). To sum up the results, the postoperative survival time of the SAMP8 mice injected with adenovirus expressing sDSS1 protein was significantly longer than that of the mice only injected with control virus. The significant difference was analyzed by ANOVA (P-value<0.01).

The above detailed description only specifies the feasible embodiments of the present application and is not intended to limit the scope of protection of the present application. Any equivalent embodiments or alterations not deviating from the gist of the present application shall be covered in the scope of protection of the present application.

SEQUENCE LISTING

```
<160> NUMBER OF SEQ ID NOS: 17

<210> SEQ ID NO 1
<211> LENGTH: 89
<212> TYPE: PRT
<213> ORGANISM: Homo sapiens
<220> FEATURE:
<223> OTHER INFORMATION: The SDSS1 amino acid sequence of Homo sapiens

<400> SEQUENCE: 1

Met Ser Glu Lys Lys Gln Pro Val Asp Leu Gly Leu Leu Glu Glu Asp
1               5                   10                  15

Asp Glu Phe Glu Glu Phe Pro Ala Glu Asp Trp Ala Gly Leu Asp Glu
            20                  25                  30

Asp Glu Asp Ala His Val Trp Glu Asp Asn Trp Asp Asp Asp Asn Val
```

```
                35                  40                  45
Glu Asp Asp Phe Ser Asn Gln Leu Arg Ala Thr Val Leu Leu Met Ile
            50                  55                  60
Leu Val Cys Glu Thr Pro Tyr Gly Cys Tyr Val Leu His Gln Lys Gly
 65                  70                  75                  80
Arg Met Cys Ser Ala Phe Leu Cys Cys
                85

<210> SEQ ID NO 2
<211> LENGTH: 31
<212> TYPE: PRT
<213> ORGANISM: Homo sapiens
<220> FEATURE:
<223> OTHER INFORMATION: C-terminal 31 amino acid sequences of the SDSS1

<400> SEQUENCE: 2

Thr Val Leu Leu Met Ile Leu Val Cys Glu Thr Pro Tyr Gly Cys Tyr
 1               5                  10                  15
Val Leu His Gln Lys Gly Arg Met Cys Ser Ala Phe Leu Cys Cys
            20                  25                  30

<210> SEQ ID NO 3
<211> LENGTH: 58
<212> TYPE: PRT
<213> ORGANISM: Homo sapiens
<220> FEATURE:
<223> OTHER INFORMATION: N-terminal 58 amino acid sequences of the SDSS1

<400> SEQUENCE: 3

Met Ser Glu Lys Lys Gln Pro Val Asp Leu Gly Leu Leu Glu Glu Asp
 1               5                  10                  15
Asp Glu Phe Glu Glu Phe Pro Ala Glu Asp Trp Ala Gly Leu Asp Glu
            20                  25                  30
Asp Glu Asp Ala His Val Trp Glu Asp Asn Trp Asp Asp Asp Asn Val
         35                  40                  45
Glu Asp Asp Phe Ser Asn Gln Leu Arg Ala
     50                  55

<210> SEQ ID NO 4
<211> LENGTH: 70
<212> TYPE: PRT
<213> ORGANISM: Homo sapiens
<220> FEATURE:
<223> OTHER INFORMATION: The DSS1 amino acid sequence of Homo sapiens

<400> SEQUENCE: 4

Met Ser Glu Lys Lys Gln Pro Val Asp Leu Gly Leu Leu Glu Glu Asp
 1               5                  10                  15
Asp Glu Phe Glu Glu Phe Pro Ala Glu Asp Trp Ala Gly Leu Asp Glu
            20                  25                  30
Asp Glu Asp Ala His Val Trp Glu Asp Asn Trp Asp Asp Asp Asn Val
         35                  40                  45
Glu Asp Asp Phe Ser Asn Gln Leu Arg Ala Glu Leu Glu Lys His Gly
     50                  55                  60
Tyr Lys Met Glu Thr Ser
 65                  70

<210> SEQ ID NO 5
<211> LENGTH: 89
<212> TYPE: PRT
<213> ORGANISM: Pan troglodytes
```

<220> FEATURE:
<223> OTHER INFORMATION: The SDSS1 amino acid sequence of Pan
      troglodytes

<400> SEQUENCE: 5

```
Met Ser Glu Lys Lys Gln Pro Val Asp Leu Gly Leu Glu Glu Asp
1               5                   10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asn Val
                35                  40                  45

Glu Asp Asp Phe Ser Asn Gln Leu Arg Ala Thr Val Leu Leu Met Ile
 50                  55                  60

Leu Val Cys Glu Thr Pro Tyr Gly Cys Tyr Val Leu His Gln Lys Gly
 65                  70                  75                  80

Arg Met Cys Ser Ala Phe Leu Cys Cys
                 85
```

<210> SEQ ID NO 6
<211> LENGTH: 89
<212> TYPE: PRT
<213> ORGANISM: Pan paniscus
<220> FEATURE:
<223> OTHER INFORMATION: The SDSS1 amino acid sequence of Pan paniscus

<400> SEQUENCE: 6

```
Met Ser Glu Lys Lys Gln Pro Val Asp Leu Gly Leu Glu Glu Asp
1               5                   10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asn Val
                35                  40                  45

Glu Asp Asp Phe Ser Asn Gln Leu Arg Ala Thr Val Leu Leu Met Ile
 50                  55                  60

Leu Val Cys Glu Thr Pro Tyr Gly Cys Tyr Val Leu His Gln Lys Gly
 65                  70                  75                  80

Arg Met Cys Ser Ala Phe Leu Cys Cys
                 85
```

<210> SEQ ID NO 7
<211> LENGTH: 89
<212> TYPE: PRT
<213> ORGANISM: Gorilla gorilla
<220> FEATURE:
<223> OTHER INFORMATION: The SDSS1 amino acid sequence of Gorilla
      gorilla

<400> SEQUENCE: 7

```
Met Ser Glu Lys Lys Gln Pro Val Asp Leu Gly Leu Glu Glu Asp
1               5                   10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asn Val
                35                  40                  45

Glu Asp Asp Phe Ser Asn Gln Leu Arg Val Thr Val Leu Leu Met Ile
 50                  55                  60

Leu Val Cys Glu Thr Leu Tyr Gly Cys Tyr Val Leu His Gln Lys Gly
 65                  70                  75                  80

Arg Met Cys Ser Ala Phe Leu Cys Cys
```

-continued

```
                85

<210> SEQ ID NO 8
<211> LENGTH: 89
<212> TYPE: PRT
<213> ORGANISM: Pongo abelii
<220> FEATURE:
<223> OTHER INFORMATION: The SDSS1 amino acid sequence of Pongo abelii

<400> SEQUENCE: 8

Met Ser Glu Lys Lys Gln Pro Val Asp Leu Gly Leu Leu Glu Glu Asp
1               5                  10                  15

Asp Glu Phe Glu Glu Phe Pro Ala Glu Asp Trp Ala Gly Leu Asp Glu
            20                  25                  30

Asp Glu Asp Ala His Val Trp Glu Asp Asn Trp Asp Asp Asn Val
        35                  40                  45

Glu Asp Asp Phe Ser Asn Gln Leu Arg Ala Thr Ile Leu Leu Met Ile
    50                  55                  60

Leu Val Cys Glu Thr Pro Tyr Gly Cys Tyr Val Leu His Gln Lys Gly
65                  70                  75                  80

Arg Met Cys Ser Ala Phe Leu Cys Cys
                85

<210> SEQ ID NO 9
<211> LENGTH: 89
<212> TYPE: PRT
<213> ORGANISM: Pongo Nomascus leucogenys
<220> FEATURE:
<223> OTHER INFORMATION: The SDSS1 amino acid sequence of Pongo Nomascus
      leucogenys

<400> SEQUENCE: 9

Met Ser Glu Lys Lys Gln Pro Val Asp Leu Gly Leu Leu Glu Glu Asp
1               5                  10                  15

Asp Glu Phe Glu Glu Phe Pro Ala Glu Asp Trp Ala Gly Leu Asp Glu
            20                  25                  30

Asp Glu Asp Ala His Val Trp Glu Asp Asn Trp Asp Asp Asn Val
        35                  40                  45

Glu Asp Asp Phe Ser Asn Gln Leu Arg Ala Thr Val Leu Leu Met Val
    50                  55                  60

Leu Val Cys Glu Thr Pro Tyr Gly Cys Tyr Val Leu His Gln Lys Glu
65                  70                  75                  80

Arg Met Cys Ser Ala Phe Leu Cys Cys
                85

<210> SEQ ID NO 10
<211> LENGTH: 89
<212> TYPE: PRT
<213> ORGANISM: Rhinopithecus roxellana
<220> FEATURE:
<223> OTHER INFORMATION: The SDSS1 amino acid sequence of Rhinopithecus
      roxellana

<400> SEQUENCE: 10

Met Ser Glu Lys Lys Gln Pro Val Asp Leu Gly Leu Leu Glu Glu Asp
1               5                  10                  15

Asp Glu Phe Glu Glu Phe Pro Ala Glu Asp Trp Ala Gly Leu Asp Glu
            20                  25                  30

Asp Glu Asp Ala His Val Trp Glu Asp Asn Trp Asp Asp Asn Val
        35                  40                  45
```

```
Glu Asp Asp Phe Ser Asn Gln Leu Arg Ala Thr Val Leu Leu Met Ile
        50                  55                  60

Lys Val Tyr Glu Thr Pro Tyr Gly Cys Tyr Ile Leu His Gln Lys Gly
 65                  70                  75                  80

Arg Met Cys Ser Ala Phe Leu Cys Cys
                85

<210> SEQ ID NO 11
<211> LENGTH: 89
<212> TYPE: PRT
<213> ORGANISM: Macaca mulatta
<220> FEATURE:
<223> OTHER INFORMATION: The SDSS1 amino acid sequence of Macaca mulatta

<400> SEQUENCE: 11

Met Ser Glu Lys Lys Gln Pro Val Asp Leu Gly Leu Leu Glu Glu Asp
 1               5                  10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asp Asn Val
            35                  40                  45

Glu Asp Asp Phe Ser Asn Gln Leu Arg Ala Thr Val Leu Leu Met Ile
        50                  55                  60

Lys Val Tyr Glu Thr Pro Tyr Gly Cys Tyr Ile Leu His Gln Lys Gly
 65                  70                  75                  80

Arg Met Cys Ser Ala Phe Leu Cys Cys
                85

<210> SEQ ID NO 12
<211> LENGTH: 89
<212> TYPE: PRT
<213> ORGANISM: Papio anubis
<220> FEATURE:
<223> OTHER INFORMATION: The SDSS1 amino acid sequence of Papio anubis

<400> SEQUENCE: 12

Met Ser Glu Lys Lys Gln Pro Val Asp Leu Gly Leu Leu Glu Glu Asp
 1               5                  10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asp Asn Val
            35                  40                  45

Glu Asp Asp Phe Ser Asn Gln Leu Arg Ala Thr Val Leu Leu Met Ile
        50                  55                  60

Lys Val Tyr Glu Thr Pro Tyr Gly Cys Tyr Ile Leu His Gln Lys Gly
 65                  70                  75                  80

Arg Met Cys Ser Ala Phe Leu Cys Cys
                85

<210> SEQ ID NO 13
<211> LENGTH: 89
<212> TYPE: PRT
<213> ORGANISM: Papio Colobus angolensis
<220> FEATURE:
<223> OTHER INFORMATION: The SDSS1 amino acid sequence of Papio Colobus
      angolensis

<400> SEQUENCE: 13

Met Ser Glu Lys Lys Gln Pro Val Asp Leu Gly Leu Leu Glu Glu Asp
 1               5                  10                  15
```

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asn Val
            35                  40                  45

Glu Asp Asp Phe Ser Asn Gln Leu Arg Ala Thr Val Leu Leu Met Lys
 50                  55                  60

Lys Val Tyr Glu Thr Pro Tyr Gly Cys Tyr Ile Leu His Gln Lys Gly
 65                  70                  75                  80

Arg Met Cys Ser Ala Phe Leu Cys Cys
                85

<210> SEQ ID NO 14
<211> LENGTH: 89
<212> TYPE: PRT
<213> ORGANISM: Cercocebus atys
<220> FEATURE:
<223> OTHER INFORMATION: The SDSS1 amino acid sequence of Cercocebus
      atys

<400> SEQUENCE: 14

Met Ser Glu Lys Lys Gln Pro Val Asp Leu Gly Leu Glu Glu Asp
 1               5                  10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asn Val
            35                  40                  45

Glu Asp Asp Phe Ser Asn Gln Leu Arg Ala Thr Val Leu Leu Met Ile
 50                  55                  60

Lys Val Tyr Glu Thr Pro Tyr Gly Cys Tyr Ile Leu His Gln Lys Gly
 65                  70                  75                  80

Arg Met Cys Ser Ala Phe Leu Cys Cys
                85

<210> SEQ ID NO 15
<211> LENGTH: 89
<212> TYPE: PRT
<213> ORGANISM: Mandrillus leucophaeus
<220> FEATURE:
<223> OTHER INFORMATION: The SDSS1 amino acid sequence of Mandrillus
      leucophaeus

<400> SEQUENCE: 15

Met Ser Glu Lys Lys Gln Pro Val Asp Leu Gly Leu Glu Glu Asp
 1               5                  10                  15

Asp Glu Phe Glu Glu Phe Pro Ala Glu Asp Trp Ala Gly Leu Asp Glu
                20                  25                  30

Asp Glu Asp Ala His Val Trp Glu Asp Asn Trp Asp Asp Asn Val
            35                  40                  45

Glu Asp Asp Phe Ser Asn Gln Leu Arg Ala Thr Val Leu Leu Met Ile
 50                  55                  60

Lys Val Tyr Glu Thr Pro Tyr Gly Cys Tyr Ile Leu His Gln Lys Gly
 65                  70                  75                  80

Arg Met Cys Ser Ala Phe Leu Cys Cys
                85

<210> SEQ ID NO 16
<211> LENGTH: 89
<212> TYPE: PRT
<213> ORGANISM: Macaca nemestrina
<220> FEATURE:

```
<223> OTHER INFORMATION: The SDSS1 amino acid sequence of Macaca
      nemestrina

<400> SEQUENCE: